(12) United States Patent
Zaiou et al.

(10) Patent No.: US 7,173,007 B1
(45) Date of Patent: Feb. 6, 2007

(54) THERAPY FOR MICROBIAL INFECTIONS

(75) Inventors: Mohamed Zaiou, Saulxures-les-Nancy (FR); Richard L. Gallo, San Diego, CA (US); Victor Nizet, San Diego, CA (US)

(73) Assignees: The Regents of the University of California, California; The United States of America as represented by the Department of Veteran Affairs, Washington, DC (US)

( * ) Notice: Subject to any disclaimer, the term of this patent is extended or adjusted under 35 U.S.C. 154(b) by 120 days.

(21) Appl. No.: 10/815,562

(22) Filed: Mar. 31, 2004

Related U.S. Application Data

(60) Provisional application No. 60/459,924, filed on Apr. 2, 2003.

(51) Int. Cl.
  *A61K 38/00* (2006.01)
(52) U.S. Cl. .................... 514/12; 514/2; 530/300; 530/350; 435/440; 435/69.1
(58) Field of Classification Search ............. 530/300, 530/350; 514/2, 12; 435/440, 69.1
See application file for complete search history.

(56) References Cited

U.S. PATENT DOCUMENTS 4,482,680 A   11/1984   Sheldon
5,618,675 A   4/1997   Larrick
6,040,291 A   3/2000   Hirata
2003/0022829 A1   1/2003   Maury

FOREIGN PATENT DOCUMENTS

| EP | 1 358 888 A1 | 11/2003 |
| SE | WO96/08508 A1 * | 3/1996 |
| WO | WO 02/13857 | 2/2002 |
| WO | WO 02/060468 A2 | 8/2002 |

OTHER PUBLICATIONS

Boman et al. "Prepro-FALL-99" Jun. 6, 1996, Database: A_Geneseq_21, Accession No. AAR92924, alignment result 4.*
Benincasa et al., "In vitro and in vivo antimicrobial activity of two alpha-helical cathelicidin peptides and of their synthetic analogs," Peptides, vol. 24, No. 11, pp. 1723-1731, Nov. 2003.
Gallo et al., "Identification of CRAMP, a cathelin-related antimicriobial peptide expressed in the embryonic and adult mouse," J. Biol. Chem., vol. 272, No. 20, pp. 13088-13093, May 16, 1997.
Gennaro et al., "Pro-rich antimicrobial peptides from animals: structure, biological functions and mechanism of action," Curr. Pharm. Des. vol. 8, No. 9, pp. 763-778, 2002.

(Continued)

*Primary Examiner*—Jon Weber
*Assistant Examiner*—Rita Mitra
(74) *Attorney, Agent, or Firm*—Buchanan Ingersoll & Rooney, LLP

(57) ABSTRACT

The disclosure provides a novel class of cationic cathelin-like peptides and polypeptides that have antimicrobial activity. These peptides are useful for inhibiting microbial infection or growth.

11 Claims, 6 Drawing Sheets

OTHER PUBLICATIONS

Gennaro et al., "Structural features and biological activities of the cathelicidin-derived antimicrobial peptides," Biopolymers, vol. 55, No. 1, pp. 31-49, 2000..

Gennaro et al. "Biological characterization of a novel mammalian antimicrobial peptide," Biochim Biophys Acta, vol. 1425, No. 2, pp. 361-368, Oct. 23, 1998.

Ha et al., "Synthesis and Antibioteic Activities of CRAMP, a Cathelin-related Antimicrobial Peptide and Its Fragments," Bull. Korean Chem. Soc., vol. 20, No. 9, pp. 1073-1077, 1999.

Howell et al., "Selective Killing of Vaccinia Virus by LL-37: Implications for Eczema Vaccinatum," J. of Immunol., vol. 172, pp. 1763-1767, 2004.

Ong et al., "Endogenous Antimicrobial Peptides And Skin Infections In Atopic Dermatitis," N Engl. J. Med., vol. 347, No. 15, pp. 1151-1160, Oct. 10, 2002.

Sanchez et al., "Overexpression and structural study of the cathelicidin motif of the protegrin-3 precursor," Biochemistry, vol. 41, No. 1, pp. 21-30, Jan. 8, 2002.

Skerlavaj et al., "Structural and functional analysis of horse cathelicidin peptides," Antimicrob. Agents Chemother., vol. 45, No. 3, pp. 715-722, Mar. 2001.

Tjabringa et al., "The Antimicrobial Peptide LL-37 Activates Innate Immunity at the Airway Epithelial Surface by Transactivation of the Epidermal Growth Factor Receptor," J. or Immunol., vol. 171, pp. 6690-6696, 2003.

Zaiou et al., "Antimicrobial and Protease Inhibitory Functions of the Human Cathelicidin (hCAP18/LL-37) Prosequence," J. of Invest. Derm., vol. 120, No. 5, pp. 810-816, May 2003.

Zanetti et al., "Cathelicidin peptides as candidates for a novel class of antimicrobials," Curr. Pharm. Des., vol. 8, No. 9, pp. 779-793, 2002.

Zanetti et al., "Structure and biology of cathelicidins," Adv. Exp. Med. Biol., vol. 479, pp. 203-218, 2000.

Zanetti et al., "The cathelicidin family of antimicrobial peptide precursors: a component of the oxygen-independent defense mechanisms of neutrophils," Ann. N. Y. Acad. Sci., vol. 832, pp. 147-162, Dec. 15, 1997.

Zanetti, Margherita; Renato Gennaro, Barbara Skerlavaj; Linda Tomasinsig and Raffaella Circo; "Cathelicidin Peptides as Candidates for a Novel Class of Antimicrobials" Current Pharaceutical Design, 2002, vol. 8, No. 9, pp. 779-793.

Smeianov, Vladimir; Kellie Scott, and Gregor Reid; "Activity of Cecropin P1 and FA-LL-37 Against Urogenital Microflora" Microbes and Infections, 2000, vol. 2, pp. 773-777.

Johansson, Jan; Gudmundur H. Gudmundsson; Martin E. Rottenberg; Kurt D. Berndt; and Birgitta Agerberth; "Conformation-dependent Antibacterial Activity of the Naturally Occurring Human Peptide LL-37" The Journal of Biological Chemistry; vol. 273, No. 6, Feb. 6, 1998, pp. 3718-3724.

\* cited by examiner

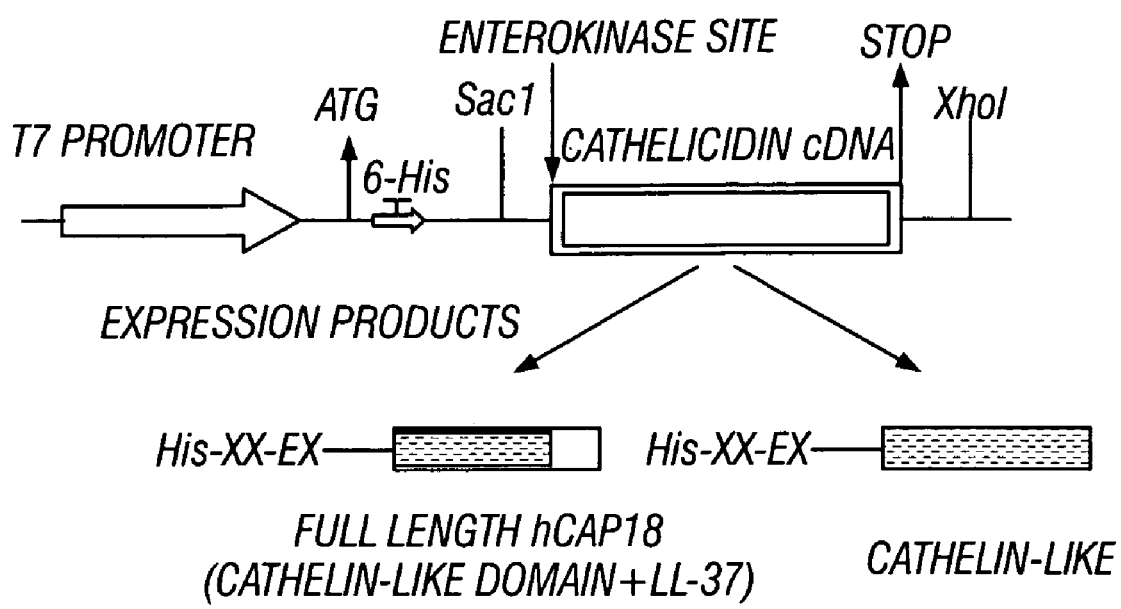
FIG. 1A
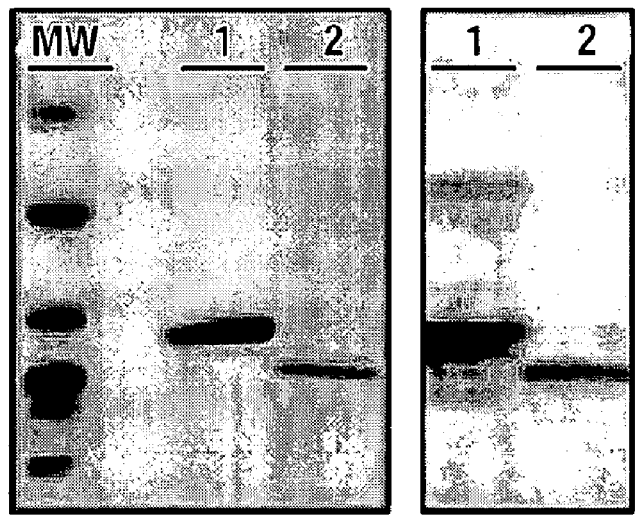
FIG. 1B     FIG. 1C

FIG. 5

SEQUENCE LISTING

<160> NUMBER OF SEQ ID NOS: 16

<210> SEQ ID NO 1
<211> LENGTH: 513
<212> TYPE: DNA
<213> ORGANISM: Homo sapiens

<400> SEQUENCE: 1

```
atgaagaccc aaagggatgg ccactccctg gggcggtggt cactggtgct cctgctgctg      60
ggcctggtga tgcctctggc catcattgcc caggtcctca gctacaagga agctgtgctt     120
cgtgctatag atggcatcaa ccagcggtcc tcggatgcta acctctaccg cctcctggac     180
ctggacccca ggcccacgat ggatggggac ccagacacgc caaagcctgt gagcttcaca     240
gtgaaggaga cagtgtgccc caggacgaca cagcagtcac cagaggattg tgacttcaag     300
aaggacgggc tggtgaagcg cgtgtatggg acagtgacce tcaaccaggc caggggctcc     360
tttgacatca gttgtgataa ggataacaag agatttgccc tgctgggtga tttcttccgg     420
aaatctaaag agaagattgg caaagagttt aaaagaattg tccagagaat caaggatttt     480
ttgcggaatc ttgtacccag gacagagtcc tag                                  513
```

<210> SEQ ID NO 2
<211> LENGTH: 170
<212> TYPE: PRT
<213> ORGANISM: Homo sapiens

<400> SEQUENCE: 2

```
Met Lys Thr Gln Arg Asp Gly His Ser Leu Gly Arg Trp Ser Leu Val
 1               5                  10                  15

Leu Leu Leu Leu Gly Leu Val Met Pro Leu Ala Ile Ile Ala Gln Val
                20                  25                  30

Leu Ser Tyr Lys Glu Ala Val Leu Arg Ala Ile Asp Gly Ile Asn Gln
            35                  40                  45

Arg Ser Ser Asp Ala Asn Leu Tyr Arg Leu Leu Asp Leu Asp Pro Arg
        50                  55                  60

Pro Thr Met Asp Gly Asp Pro Asp Thr Pro Lys Pro Val Ser Phe Thr
65                  70                  75                  80

Val Lys Glu Thr Val Cys Pro Arg Thr Thr Gln Gln Ser Pro Glu Asp
                85                  90                  95

Cys Asp Phe Lys Lys Asp Gly Leu Val Lys Arg Cys Met Gly Thr Val
                100                 105                 110

Thr Leu Asn Gln Ala Arg Gly Ser Phe Asp Ile Ser Cys Asp Lys Asp
            115                 120                 125

Asn Lys Arg Phe Ala Leu Leu Gly Asp Phe Arg Lys Ser Lys Glu
        130                 135                 140

Lys Ile Gly Lys Glu Phe Lys Arg Ile Val Gln Arg Ile Lys Asp Phe
145                 150                 155                 160

Leu Arg Asn Leu Val Pro Arg Thr Glu Ser
                165                 170
```

```
<210> SEQ ID NO 3
<211> LENGTH: 103
<212> TYPE: PRT
<213> ORGANISM: Artificial Sequence
<220> FEATURE:
<223> OTHER INFORMATION: cationic cathelin-like peptide
<220> FEATURE:
<221> NAME/KEY: VARIANT
<222> LOCATION: 1
<223> OTHER INFORMATION: Xaa = Gln or Arg
<220> FEATURE:
<221> NAME/KEY: VARIANT
<222> LOCATION: 2
<223> OTHER INFORMATION: Xaa = Ala, Val or Thr
<220> FEATURE:
<221> NAME/KEY: VARIANT
<222> LOCATION: 3
<223> OTHER INFORMATION: Xaa = Leu or Pro
<220> FEATURE:
<221> NAME/KEY: VARIANT
<222> LOCATION: 6
<223> OTHER INFORMATION: Xaa = Lys or Arg
<220> FEATURE:
<221> NAME/KEY: VARIANT
<222> LOCATION: 7
<223> OTHER INFORMATION: Xaa = Glu or Asp
<220> FEATURE:
<221> NAME/KEY: VARIANT
<222> LOCATION: 13
<223> OTHER INFORMATION: Xaa = Val or Ile
<220> FEATURE:
<221> NAME/KEY: VARIANT
<222> LOCATION: 14
<223> OTHER INFORMATION: Xaa = Asn, Asp or Gly
<220> FEATURE:
<221> NAME/KEY: VARIANT
<222> LOCATION: 15
<223> OTHER INFORMATION: Xaa = Gly, Arg, Asp or Gln
<220> FEATURE:
<221> NAME/KEY: VARIANT
<222> LOCATION: 16
<223> OTHER INFORMATION: Xaa = Leu, Ile or Phe
<220> FEATURE:
<221> NAME/KEY: VARIANT
<222> LOCATION: 18
<223> OTHER INFORMATION: Xaa = Glu or Gln
<220> FEATURE:
<221> NAME/KEY: VARIANT
<222> LOCATION: 19
<223> OTHER INFORMATION: Xaa = Gln or Arg
<220> FEATURE:
<221> NAME/KEY: VARIANT
<222> LOCATION: 21
<223> OTHER INFORMATION: Xaa = Ser or Leu
<220> FEATURE:
<221> NAME/KEY: VARIANT
<222> LOCATION: 22
<223> OTHER INFORMATION: Xaa = Asp or Glu
<220> FEATURE:
<221> NAME/KEY: VARIANT
<222> LOCATION: 23
<223> OTHER INFORMATION: Xaa = Glu, Ala or Thr
<220> FEATURE:
<221> NAME/KEY: VARIANT
<222> LOCATION: 30
<223> OTHER INFORMATION: Xaa = Gln, Glu or Asp
<220> FEATURE:
<221> NAME/KEY: VARIANT
<222> LOCATION: 32
<223> OTHER INFORMATION: Xaa = Asp or Asn
<220> FEATURE:
<221> NAME/KEY: VARIANT
<222> LOCATION: 33
<223> OTHER INFORMATION: Xaa = Ser, Gln or Pro
<220> FEATURE:
<221> NAME/KEY: VARIANT
<222> LOCATION: 34
<223> OTHER INFORMATION: Xaa = Gln, Pro, Arg, Glu or Ala
<220> FEATURE:
```

```
<221> NAME/KEY: VARIANT
<222> LOCATION: 36
<223> OTHER INFORMATION: Xaa = Lys, Thr, Gln or Asn
<220> FEATURE:
<221> NAME/KEY: VARIANT
<222> LOCATION: 37
<223> OTHER INFORMATION: Xaa = Gly, Ala, Met or Asp
<220> FEATURE:
<221> NAME/KEY: VARIANT
<222> LOCATION: 38
<223> OTHER INFORMATION: Xaa = Asp or Glu
<220> FEATURE:
<221> NAME/KEY: VARIANT
<222> LOCATION: 39
<223> OTHER INFORMATION: Xaa = Gly, Glu or Val
<220> FEATURE:
<221> NAME/KEY: VARIANT
<222> LOCATION: 42
<223> OTHER INFORMATION: Xaa = Asn, Gly or Asp
<220> FEATURE:
<221> NAME/KEY: VARIANT
<222> LOCATION: 43
<223> OTHER INFORMATION: Xaa = Thr or Ile
<220> FEATURE:
<221> NAME/KEY: VARIANT
<222> LOCATION: 44
<223> OTHER INFORMATION: Xaa = Pro or Arg
<220> FEATURE:
<221> NAME/KEY: VARIANT
<222> LOCATION: 46
<223> OTHER INFORMATION: Xaa = Pro or Ser
<220> FEATURE:
<221> NAME/KEY: VARIANT
<222> LOCATION: 48
<223> OTHER INFORMATION: Xaa = Ser or Arg
<220> FEATURE:
<221> NAME/KEY: VARIANT
<222> LOCATION: 50
<223> OTHER INFORMATION: Xaa = Thr or Arg
<220> FEATURE:
<221> NAME/KEY: VARIANT
<222> LOCATION: 57
<223> OTHER INFORMATION: Xaa = Pro or Gly
<220> FEATURE:
<221> NAME/KEY: VARIANT
<222> LOCATION: 58
<223> OTHER INFORMATION: Xaa = Lys or Arg
<220> FEATURE:
<221> NAME/KEY: VARIANT
<222> LOCATION: 59
<223> OTHER INFORMATION: Xaa = Pro, Thr or Ala
<220> FEATURE:
<221> NAME/KEY: VARIANT
<222> LOCATION: 60
<223> OTHER INFORMATION: Xaa = Thr or Glu
<220> FEATURE:
<221> NAME/KEY: VARIANT
<222> LOCATION: 61
<223> OTHER INFORMATION: Xaa = Gln or Arg
<220> FEATURE:
<221> NAME/KEY: VARIANT
<222> LOCATION: 63
<223> OTHER INFORMATION: Xaa = Pro, Ser or Leu
<220> FEATURE:
<221> NAME/KEY: VARIANT
<222> LOCATION: 64
<223> OTHER INFORMATION: Xaa = Pro or Leu
<220> FEATURE:
<221> NAME/KEY: VARIANT
<222> LOCATION: 66
<223> OTHER INFORMATION: Xaa = Gln, Leu, Asp or Glu
<220> FEATURE:
<221> NAME/KEY: VARIANT
<222> LOCATION: 68
<223> OTHER INFORMATION: Xaa = Gly, Asp or Ala
<220> FEATURE:
<221> NAME/KEY: VARIANT
<222> LOCATION: 71
<223> OTHER INFORMATION: Xaa = Asp, Glu or Lys
```

-continued

```
<220> FEATURE:
<221> NAME/KEY: VARIANT
<222> LOCATION: 72
<223> OTHER INFORMATION: Xaa = Asn, Asp or Gln
<220> FEATURE:
<221> NAME/KEY: VARIANT
<222> LOCATION: 74
<223> OTHER INFORMATION: Xaa = Leu or Arg
<220> FEATURE:
<221> NAME/KEY: VARIANT
<222> LOCATION: 77
<223> OTHER INFORMATION: Xaa = Gln or Arg
<220> FEATURE:
<221> NAME/KEY: VARIANT
<222> LOCATION: 79
<223> OTHER INFORMATION: Xaa = Glu, Val or Met
<220> FEATURE:
<221> NAME/KEY: VARIANT
<222> LOCATION: 81
<223> OTHER INFORMATION: Xaa = Ala or Thr
<220> FEATURE:
<221> NAME/KEY: VARIANT
<222> LOCATION: 83
<223> OTHER INFORMATION: Xaa = Thr or Ile
<220> FEATURE:
<221> NAME/KEY: VARIANT
<222> LOCATION: 85
<223> OTHER INFORMATION: Xaa = Asp or Asn
<220> FEATURE:
<221> NAME/KEY: VARIANT
<222> LOCATION: 86
<223> OTHER INFORMATION: Xaa = Glu, Pro or Gln
<220> FEATURE:
<221> NAME/KEY: VARIANT
<222> LOCATION: 87
<223> OTHER INFORMATION: Xaa = Asp, Ser or Ala
<220> FEATURE:
<221> NAME/KEY: VARIANT
<222> LOCATION: 88
<223> OTHER INFORMATION: Xaa = Thr, Ile, Arg, Ala or Asn
<220> FEATURE:
<221> NAME/KEY: VARIANT
<222> LOCATION: 89
<223> OTHER INFORMATION: Xaa = Gly, His or Asp
<220> FEATURE:
<221> NAME/KEY: VARIANT
<222> LOCATION: 90
<223> OTHER INFORMATION: Xaa = Ser, Tyr or Gln
<220> FEATURE:
<221> NAME/KEY: VARIANT
<222> LOCATION: 91
<223> OTHER INFORMATION: Xaa = Phe or Leu
<220> FEATURE:
<221> NAME/KEY: VARIANT
<222> LOCATION: 93
<223> OTHER INFORMATION: Xaa = Ile or Leu
<220> FEATURE:
<221> NAME/KEY: VARIANT
<222> LOCATION: 94
<223> OTHER INFORMATION: Xaa = Asn or Ser
<220> FEATURE:
<221> NAME/KEY: VARIANT
<222> LOCATION: 96
<223> OTHER INFORMATION: Xaa = Asn or Asp
<220> FEATURE:
<221> NAME/KEY: VARIANT
<222> LOCATION: 97
<223> OTHER INFORMATION: Xaa = Ser, Glu or Lys
<220> FEATURE:
<221> NAME/KEY: VARIANT
<222> LOCATION: 98
<223> OTHER INFORMATION: Xaa = Ile, Asp, Ala or Leu
<220> FEATURE:
<221> NAME/KEY: VARIANT
<222> LOCATION: 99
<223> OTHER INFORMATION: Xaa = Leu, Gln or Asn
<220> FEATURE:
<221> NAME/KEY: VARIANT
<222> LOCATION: 100
```

```
<223> OTHER INFORMATION: Xaa = Ser, Pro, Lys or Gln
<220> FEATURE:
<221> NAME/KEY: VARIANT
<222> LOCATION: 101
<223> OTHER INFORMATION: Xaa = Val, Phe or Arg
<220> FEATURE:
<221> NAME/KEY: VARIANT
<222> LOCATION: 102
<223> OTHER INFORMATION: Xaa = Arg, Phe or Lys
<220> FEATURE:
<221> NAME/KEY: VARIANT
<222> LOCATION: 103
<223> OTHER INFORMATION: Xaa = Phe, Ala, Arg or Lys

<400> SEQUENCE: 3

Xaa Xaa Xaa Ser Tyr Xaa Xaa Ala Val Leu Arg Ala Xaa Xaa Xaa Xaa
 1               5                  10                  15

Asn Xaa Xaa Ser Xaa Xaa Xaa Asn Leu Tyr Arg Leu Leu Xaa Leu Xaa
             20                  25                  30

Xaa Xaa Pro Xaa Xaa Xaa Xaa Asp Pro Xaa Xaa Xaa Lys Xaa Val Xaa
         35                  40                  45

Phe Xaa Val Lys Glu Thr Val Cys Xaa Xaa Xaa Xaa Xaa Gln Xaa Xaa
     50                  55                  60

Glu Xaa Cys Xaa Phe Lys Xaa Xaa Gly Xaa Val Lys Xaa Cys Xaa Gly
65                  70                  75                  80

Xaa Val Xaa Leu Xaa Xaa Xaa Xaa Xaa Xaa Asp Xaa Xaa Cys Xaa
             85                  90                  95

Xaa Xaa Xaa Xaa Xaa Xaa Xaa
         100

<210> SEQ ID NO 4
<211> LENGTH: 5
<212> TYPE: PRT
<213> ORGANISM: Artificial Sequence
<220> FEATURE:
<223> OTHER INFORMATION: spacer peptide

<400> SEQUENCE: 4

Gly Gly Gly Gly Ser
 1               5

<210> SEQ ID NO 5
<211> LENGTH: 22
<212> TYPE: PRT
<213> ORGANISM: Artificial Sequence
<220> FEATURE:
<223> OTHER INFORMATION: linker moiety

<400> SEQUENCE: 5

Gly Gly Gly Gly Gly Gly Ser Met Phe Gly Gly Ala Lys Lys Arg Ser
 1               5                  10                  15

Gly Gly Gly Gly Gly Gly
             20

<210> SEQ ID NO 6
<211> LENGTH: 45
<212> TYPE: DNA
<213> ORGANISM: Artificial Sequence
<220> FEATURE:
<223> OTHER INFORMATION: primer

<400> SEQUENCE: 6
tccgagctcg acgatgacga taagctgctg ggtgatttct tccgg          45
```

```
<210> SEQ ID NO 7
<211> LENGTH: 39
<212> TYPE: DNA
<213> ORGANISM: Artificial Sequence
<220> FEATURE:
<223> OTHER INFORMATION: primer

<400> SEQUENCE: 7
ccgctcgagc taggactctg tcctgggtac aagattccg                39

<210> SEQ ID NO 8
<211> LENGTH: 36
<212> TYPE: DNA
<213> ORGANISM: Artificial Sequence
<220> FEATURE:
<223> OTHER INFORMATION: primer

<400> SEQUENCE: 8
ccgctcgagc tactaggcaa atctcttgtt atcctt                   36

<210> SEQ ID NO 9
<211> LENGTH: 5
<212> TYPE: PRT
<213> ORGANISM: Artificial Sequence
<220> FEATURE:
<223> OTHER INFORMATION: recognition sequence

<400> SEQUENCE: 9

Asp Asp Asp Asp Lys
1               5

<210> SEQ ID NO 10
<211> LENGTH: 5
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 2, 4
<223> OTHER INFORMATION: Xaa = Any Amino Acid

<400> SEQUENCE: 10

Gln Xaa Val Xaa Gly
1               5

<210> SEQ ID NO 11
<211> LENGTH: 172
<212> TYPE: PRT
<213> ORGANISM: Canis familiaris

<400> SEQUENCE: 11

Met Glu Thr Gln Lys Asp Ser Pro Ser Leu Gly Arg Trp Ser Leu Leu
1               5                   10                  15

Leu Leu Leu Leu Gly Leu Val Ile Thr Pro Ala Ala Ser Arg Ala Leu
            20                  25                  30

Ser Tyr Arg Glu Ala Val Leu Arg Ala Val Asn Gly Phe Asn Gln Arg
        35                  40                  45

Ser Ser Glu Glu Asn Leu Tyr Arg Leu Leu Gln Leu Asn Ser Gln Pro
    50                  55                  60

Lys Gly Asp Glu Asp Pro Asn Ile Pro Lys Pro Val Ser Phe Thr Val
65                  70                  75                  80

Lys Glu Thr Val Cys Pro Lys Thr Thr Gln Gln Pro Leu Glu Gln Cys
                85                  90                  95
```

```
Gly Phe Lys Asp Asn Gly Leu Val Lys Gln Cys Glu Gly Thr Val Ile
                100                 105                 110

Leu Asp Glu Asp Thr Gly Tyr Phe Asp Leu Asn Cys Asp Ser Ile Leu
            115                 120                 125

Gln Val Lys Lys Ile Asp Arg Leu Lys Glu Leu Ile Thr Thr Gly Ala
        130                 135                 140

Gln Lys Ile Gly Lys Lys Ile Arg Arg Ile Gly Gln Arg Ile Lys Asp
145                 150                 155                 160

Phe Leu Lys Asn Leu Gln Pro Arg Glu Glu Lys Ser
                165                 170
```

<210> SEQ ID NO 12
<211> LENGTH: 172
<212> TYPE: PRT
<213> ORGANISM: Sus scrofa

<400> SEQUENCE: 12

```
Met Glu Thr Gln Arg Ala Ser Leu Cys Leu Gly Arg Trp Ser Leu Trp
1               5                   10                  15

Leu Leu Leu Leu Ala Leu Val Val Pro Ser Ala Ser Ala Gln Ala Leu
            20                  25                  30

Ser Tyr Arg Glu Ala Val Leu Arg Ala Val Asp Arg Leu Asn Glu Gln
        35                  40                  45

Ser Ser Glu Ala Asn Leu Tyr Arg Leu Leu Glu Leu Asp Gln Pro Pro
    50                  55                  60

Lys Ala Asp Glu Asp Pro Gly Thr Pro Lys Pro Val Ser Phe Thr Val
65                  70                  75                  80

Lys Glu Thr Val Cys Pro Arg Pro Thr Arg Gln Pro Pro Glu Leu Cys
                85                  90                  95

Asp Phe Lys Glu Asn Gly Arg Val Lys Gln Cys Val Gly Thr Val Thr
                100                 105                 110

Leu Asn Pro Ser Ile His Ser Leu Asp Ile Ser Cys Asn Glu Ile Gln
            115                 120                 125

Ser Val Arg Arg Arg Pro Arg Pro Pro Tyr Leu Pro Arg Pro Arg Pro
        130                 135                 140

Pro Pro Phe Phe Pro Arg Leu Pro Arg Ile Pro Pro Gly Phe
145                 150                 155                 160

Pro Pro Arg Phe Pro Arg Phe Pro Gly Lys Arg
                165                 170
```

<210> SEQ ID NO 13
<211> LENGTH: 170
<212> TYPE: PRT
<213> ORGANISM: Homo sapiens

<400> SEQUENCE: 13

```
Met Lys Thr Gln Arg Asn Gly His Ser Leu Gly Arg Trp Ser Leu Val
1               5                   10                  15

Leu Leu Leu Leu Gly Leu Val Met Pro Leu Ala Ile Ile Ala Gln Val
            20                  25                  30

Leu Ser Tyr Lys Glu Ala Val Leu Arg Ala Ile Asp Gly Ile Asn Gln
        35                  40                  45

Arg Ser Ser Asp Ala Asn Leu Tyr Arg Leu Leu Asp Leu Asp Pro Arg
    50                  55                  60

Pro Thr Met Asp Gly Asp Pro Asp Thr Pro Lys Pro Val Ser Phe Thr
65                  70                  75                  80
```

```
Val Lys Glu Thr Val Cys Pro Arg Thr Thr Gln Gln Ser Pro Glu Asp
                85                  90                  95

Cys Asp Phe Lys Lys Asp Gly Leu Val Lys Arg Cys Met Gly Thr Val
            100                 105                 110

Thr Leu Asn Gln Ala Arg Gly Ser Phe Asp Ile Ser Cys Asp Lys Asp
        115                 120                 125

Asn Lys Arg Phe Ala Leu Leu Gly Asp Phe Arg Lys Ser Lys Glu
    130                 135                 140

Lys Ile Gly Lys Glu Phe Lys Arg Ile Val Gln Arg Ile Lys Asp Phe
145                 150                 155                 160

Leu Arg Asn Leu Val Pro Arg Thr Glu Ser
                165                 170
```

<210> SEQ ID NO 14
<211> LENGTH: 173
<212> TYPE: PRT
<213> ORGANISM: Mus musculus

<400> SEQUENCE: 14

```
Met Gln Phe Gln Arg Asp Val Pro Ser Leu Trp Leu Trp Arg Ser Leu
 1               5                  10                  15

Ser Leu Leu Leu Leu Gly Leu Gly Phe Ser Gln Thr Pro Ser Tyr
                20                  25                  30

Arg Asp Ala Val Leu Arg Ala Val Asp Asp Phe Asn Gln Gln Ser Leu
            35                  40                  45

Asp Thr Asn Leu Tyr Arg Leu Leu Asp Leu Asp Pro Glu Pro Gln Gly
    50                  55                  60

Asp Glu Asp Pro Asp Thr Pro Lys Ser Val Arg Phe Arg Val Lys Glu
65                  70                  75                  80

Thr Val Cys Gly Lys Ala Glu Arg Gln Leu Pro Glu Gln Cys Ala Phe
                85                  90                  95

Lys Glu Gln Gly Val Val Lys Gln Cys Met Gly Ala Val Thr Leu Asn
            100                 105                 110

Pro Ala Ala Asp Ser Phe Asp Ile Ser Cys Asn Glu Pro Gly Ala Gln
        115                 120                 125

Pro Phe Arg Phe Lys Lys Ile Ser Arg Leu Ala Gly Leu Leu Arg Lys
    130                 135                 140

Gly Gly Glu Lys Ile Gly Glu Lys Leu Lys Lys Ile Gly Gln Lys Ile
145                 150                 155                 160

Lys Asn Phe Phe Gln Lys Leu Val Pro Gln Pro Glu Gln
                165                 170
```

<210> SEQ ID NO 15
<211> LENGTH: 176
<212> TYPE: PRT
<213> ORGANISM: Capra hircus

<400> SEQUENCE: 15

```
Met Glu Thr Gln Gly Ala Ser Leu Ser Leu Gly Arg Trp Ser Leu Trp
 1               5                  10                  15

Leu Leu Leu Leu Gly Leu Val Val Pro Leu Ala Ser Ala Gln Ala Leu
                20                  25                  30

Ser Tyr Arg Glu Ala Val Leu Arg Ala Val Gly Gln Leu Asn Glu Arg
            35                  40                  45

Ser Ser Glu Ala Asn Leu Tyr Arg Leu Leu Glu Leu Asp Pro Ala Pro
    50                  55                  60
```

```
Asn Asp Glu Val Asp Pro Gly Thr Arg Lys Pro Val Ser Phe Thr Val
 65                  70                  75                  80

Lys Glu Thr Val Cys Pro Arg Thr Thr Gln Gln Pro Pro Glu Glu Cys
                 85                  90                  95

Asp Phe Lys Glu Asn Gly Leu Val Lys Gln Cys Val Gly Thr Val Thr
                100                 105                 110

Leu Asp Pro Ser Asn Asp Gln Phe Asp Ile Asn Cys Asn Glu Leu Gln
                115                 120                 125

Ser Val Arg Phe Arg Pro Pro Ile Arg Arg Pro Pro Ile Arg Pro Pro
130                 135                 140

Phe Asn Pro Pro Phe Arg Pro Pro Val Arg Pro Pro Phe Arg Pro Pro
145                 150                 155                 160

Phe Arg Pro Pro Phe Arg Pro Pro Ile Gly Pro Phe Pro Gly Arg Arg
                165                 170                 175

<210> SEQ ID NO 16
<211> LENGTH: 129
<212> TYPE: PRT
<213> ORGANISM: Artificial Sequence
<220> FEATURE:
<223> OTHER INFORMATION: consensus sequence

<400> SEQUENCE: 16

Met Glu Thr Gln Arg Ser Ser Leu Gly Arg Trp Ser Leu Leu Leu Leu
  1               5                  10                  15

Leu Gly Leu Val Pro Ala Ile Ala Gln Ala Leu Ser Tyr Arg Glu Ala
                 20                  25                  30

Val Leu Arg Ala Val Asp Asn Gln Arg Ser Ser Glu Ala Asn Leu Tyr
             35                  40                  45

Arg Leu Leu Leu Asp Pro Pro Asp Glu Asp Pro Thr Pro Lys Pro Val
 50                  55                  60

Ser Phe Thr Val Lys Glu Thr Val Cys Pro Arg Thr Thr Gln Gln Pro
 65                  70                  75                  80

Pro Glu Cys Asp Phe Lys Glu Asn Gly Leu Val Lys Gln Cys Gly Thr
                 85                  90                  95

Val Thr Leu Asn Pro Ser Phe Asp Ile Ser Cys Asn Glu Pro Gly Gln
                100                 105                 110

Val Arg Arg Lys Ile Gly Arg Ile Gln Arg Ile Lys Phe Leu Pro Arg
                115                 120                 125

Arg
```

THERAPY FOR MICROBIAL INFECTIONS

CROSS REFERENCE TO RELATED APPLICATIONS

This application claims priority under 35 U.S.C. §119 from Provisional Application Ser. No. 60/459,924, filed Apr. 2, 2003, the disclosure of which is incorporated herein by reference.

STATEMENT AS TO FEDERALLY-SPONSORED RESEARCH

The U.S. Government has certain rights in this disclosure pursuant to Grant Nos. AI48176 and AR45676 awarded by the National Institutes of Health.

TECHNICAL FIELD

The disclosure relates peptides that have antibiotic activity.

BACKGROUND

Small, cationic antimicrobial peptides (AMPs) are naturally occurring antibiotics of the innate immune system. AMPs are widely distributed in animals and plants and are among the most ancient host defense factors (Hofmann et al., 1999). Their spectrum of activity includes Gram-positive and Gram-negative bacteria as well as fungi and certain viruses. As resistance of pathogenic microbes to conventional antibiotics increases, researchers are exploring these endogenous antibiotics as a potential source or new therapies against variety of infectious diseases.

SUMMARY

The disclosure provides an isolated cationic cathelin-like peptide having antimicrobial activity and consisting of an amino acid sequence:

(Q/R)$X_1$(L/P)SY(K/R) (E/D)AVLRA(V/I)$X_2X_3X_4$N(E/Q)(Q/R)S(S/L)(D/E) $X_5$NLYRLL$X_6$L(D/N)$X_7X_8$P$X_9X_{10}$(D/E)$X_{11}$DP$X_{12}$(T/I)(P/R)K(P/S)V(S/R)F(T/R)VKETVC(P/G)(K/R)$X_{13}$(T/E)(Q/R)QX$_{14}$(P/L)E$X_{15}$C$X_{16}$FK$X_{17}X_{18}$G(L/R)VK(Q/R)C$X_{19}$G(A/T)V(T/I)L(D/N)$X_{20}X_{21}X_{22}X_{23}X_{24}$(F/L)D(I/L)(N/S)C(N/D)$X_{25}X_{26}X_{27}X_{28}X_{29}X_{30}X_{31}$ (SEQ ID NO:3), wherein X1 is A, V or T; X2 is N, D or G; X3 is G, R, D or Q; X4 is L, I or F; X5 is E, A or T; X6 is Q, E or D; X7 is S, Q or P; X8 is Q, P, R, E or A; X9 is K, T, Q or N; X10 is G, A, M or D; X11 is G, E or V; X12 is N, G or D; X13 is P, T or A; X14 is P, S or L; X15 is Q, L, D or E; X16 is G, D or A; X17 is D, E or K; X18 is N, D or Q; X19 is E, V or M; X20 is E, P or Q; X21 is D, S or A; X22 is T, I, R, A or N; X23 is G, H or D; X24 is S, Y or Q; X25 is S, E or K; X26 is I, D, A or L; X27 is L, Q or N; X28 is S, P, K or Q; X29 is V, F or R; X30 is R, F or K; and X31 is F, A, R or K.

The disclosure also provides a substantially purified peptide consisting of from about 96 to about 100 amino acids and including a sequence shown in SEQ ID NO:3, wherein X1 is A, V or T; X2 is N, D or G; X3 is G, R, D or Q; X4 is L, I or F; X5 is E, A or T; X6 is Q, E or D; X7 is S, Q or P; X8 is Q, P, R, E or A; X9 is K, T, Q or N; X10 is G, A, M or D; X11 is G, E or V; X12 is N, G or D; X13 is P, T or A; X14 is P, S or L; X15 is Q, L, D or E; X16 is G, D or A; X17 is D, E or K; X18 is N, D or Q; X19 is E, V or M; X20 is E, P or Q; X21 is D, S or A; X22 is T, I, R, A or N; X23 is G, H or D; X24 is S, Y or Q; X25 is S, E or K; X26 is I, D, A or L; X27 is L, Q or N; X28 is S, P, K or Q; X29 is V, F or R; X30 is R, F or K; and X31 is F, A, R or K.

Also provided by the disclosure is an isolated polynucleotide that encodes a peptide as set forth above.

The disclosure provides a method for inhibiting the growth of a bacterium or yeast comprising contacting the bacterium or yeast with an inhibiting effective amount of a peptide comprising an amino acid sequence selected from the group consisting of:

(a) (Q/R)$X_1$(L/P)SY(K/R)(E/D)AVLRA(V/I)$X_2X_3X_4$N(E/Q) (Q/R)S(S/L)(D/E)$X_5$NLYRLL$X_6$L(D/N)$X_7X_8$P$X_9X_{10}$(D/E)$X_{11}$DP$X_{12}$(T/I) (P/R)K(P/S)V(S/R)F(T/R)VKETVC(P/G)(K/R)$X_{13}$(T/E)(Q/R)QX$_{14}$(P/L)E$X_{15}$C$X_{16}$FK$X_{17}X_{18}$G(L/R)VK(Q/R)C$X_{19}$G(A/T)V(T/I)L(D/N)$X_{20}X_{21}X_{22}X_{23}X_{24}$(F/L)D(I/L) (N/S)C(N/D)$X_{25}X_{26}X_{27}X_{28}X_{29}X_{30}X_{31}$ (SEQ ID NO:3), wherein X1 is A, V or T; X2 is N, D or G; X3 is G, R, D or Q; X4 is L, I or F; X5 is E, A or T; X6 is Q, E or D; X7 is S, Q or P; X8 is Q, P, R, E or A; X9 is K, T, Q or N; X10 is G, A, M or D; X11 is G, E or V; X12 is N, G or D; X13 is P, T or A; X14 is P, S or L; X15 is Q, L, D or E; X16 is G, D or A; X17 is D, E or K; X18 is N, D or Q; X19 is E, V or M; X20 is E, P or Q; X21 is D, S or A; X22 is T, I, R, A or N; X23 is G, H or D; X24 is S, Y or Q; X25 is S, E or K; X26 is I, D, A or L; X27 is L, Q or N; X28 is S, P, K or Q; X29 is V, F or R; X30 is R, F or K; and X31 is F, A, R or K; and (b) SEQ ID NO:2 from about amino acid 31 to 131.

The disclosure also provides a pharmaceutical composition for therapy of bacterial infections and/or disorders, the composition comprising a peptide selected from the group consisting of:

(a) a peptide comprising a sequence (Q/R)$X_1$(L/P)SY(K/R) (E/D)AVLRA(V/I)$X_2X_3X_4$N(E/Q) (Q/R)S(S/L)(D/E)$X_5$NLYRLL$X_6$L(D/N)$X_7X_8$P$X_9X_{10}$(D/E)$X_{11}$DP$X_{12}$(T/I) (P/R)K(P/S)V(S/R) F(T/R)VKETVC(P/G)(K/R)$X_{13}$(T/E)(Q/R)QX$_{14}$(P/L)E$X_{15}$C$X_{16}$FK$X_{17}X_{18}$G(L/R)VK(Q/R)C$X_{19}$G(A/T)V(T/I)L(D/N)$X_{20}X_{21}X_{22}X_{23}X_{24}$(F/L)D(I/L)(N/S)C(N/D)$X_{25}X_{26}X_{27}X_{28}X_{29}X_{30}X_{31}$ (SEQ ID NO:3), wherein X1 is A, V or T; X2 is N, D or G; X3 is G, R, D or Q; X4 is L, I or F; X5 is E, A or T; X6 is Q, E or D; X7 is S, Q or P; X8 is Q, P, R, E or A; X9 is K, T, Q or N; X10 is G, A, M or D; X11 is G, E or V; X12 is N, G or D; X13 is P, T or A; X14 is P, S or L; X15 is Q, L, D or E; X16 is G, D or A; X17 is D, E or K; X18 is N, D or Q; X19 is E, V or M; X20 is E, P or Q; X21 is D, S or A; X22 is T, I, R, A or N; X23 is G, H or D; X24 is S, Y or Q; X25 is S, E or K; X26 is I, D, A or L; X27 is L, Q or N; X28 is S, P, K or Q; X29 is V, F or R; X30 is R, F or K; and X31 is F, A, R or K; and (b) a peptide comprising a sequence as set forth in SEQ ID NO:2 from about amino acid 31 to 131, in a pharmaceutically acceptable carrier.

The disclosure provides a method of alleviating symptoms of a bacterial infection in a subject, comprising administering an effective amount of an N-terminal active fragment of a cathelicidin-derived peptide comprising a sequence as set forth in SEQ ID NO:2; or a peptide comprising a sequence as set forth in SEQ ID NO:3, wherein X1 is A, V or T; X2 is N, D or G; X3 is G, R, D or Q; X4 is L, I or F; X5 is E, A or T; X6 is Q, E or D; X7 is S, Q or P; X8 is Q, P, R, E or A; X9 is K, T, Q or N; X10 is G, A, M or D; X11 is G, E or V; X12 is N, G or D; X13 is P, T or A; X14 is P, S or L; X15 is Q, L, D or E; X16 is G, D or A; X17 is D, E or K; X18 is N, D or Q; X19 is E, V or M; X20 is E, P or Q; X21 is D, S or A; X22 is T, I, R, A or N; X23 is G, H or D; X24 is S, Y or Q; X25 is S, E or K; X26 is I, D, A or L; X27 is L, Q or N; X28 is S, P, K or Q; X29 is V, F or R; X30 is R, F or K; and X31 is F, A, R or K, to the subject.

The disclosure further provides a method of promoting tissue repair and regeneration in a subject comprising contacting an injured tissue with a composition comprising a peptide selected from the group consisting of:

(a) a peptide comprising a sequence $(Q/R)X_1(L/P)SY(K/R)$ $(E/D)AVLRA(V/I)X_2X_3X_4N(E/Q)$ $(Q/R)S(S/L)(D/E)X_5NLYRLLX_6L(D/N)X_7X_8PX_9X_{10}(D/E)X_{11}DPX_{12}(T/I)$ $(P/R)K(P/S)V(S/R)F(T/R)VKETVC(P/G)(K/R)X_{13}(T/E)(Q/R)QX_{14}(P/L)$ $EX_{15}CX_{16}FKX_{17}X_{18}G(L/R)VK(Q/R)CX_{19}G(A/T)V(T/I)L(D/N)$ $X_{20}X_{21}X_{22}X_{23}X_{24}(F/L)D(I/L)(N/S)C(N/D)$ $X_{25}X_{26}X_{27}X_{28}X_{29}X_{30}X_{31}$ (SEQ ID NO:3), wherein X1 is A, V or T; X2 is N, D or G; X3 is G, R, D or Q; X4 is L, I or F; X5 is E, A or T; X6 is Q, E or D; X7 is S, Q or P; X8 is Q, P, R, E or A; X9 is K, T, Q or N; X10 is G, A, M or D; X11 is G, E or V; X12 is N, G or D; X13 is P, T or A; X14 is P, S or L; X15 is Q, L, D or E; X16 is G, D or A; X17 is D, E or K; X18 is N, D or Q; X19 is E, V or M; X20 is E, P or Q; X21 is D, S or A; X22 is T, I, R, A or N; X23 is G, H or D; X24 is S, Y or Q; X25 is S, E or K; X26 is I, D, A or L; X27 is L, Q or N; X28 is S, P, K or Q; X29 is V, F or R; X30 is R, F or K; and X31 is F, A, R or K; and (b) a peptide comprising a sequence as set forth in SEQ ID NO:2 from about amino acid 31 to 131.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

FIGS. 1A–D shows the expression and characterization of recombinant cathelicidin proteins. (a) Schematic representation of cathelicidin expression system in *E. coli*. (b) SDS-PAGE of cathelin-like protein by Coomassie blue staining; MW, molecular weight markers (from top to bottom: 45K; 30K; 20.1K; 14.3K; 6.5K; 3.5K; 2.5K); lanes 1 and 2 are cathelin-like protein before and after digestion with enterokinase. (c) Western blot analysis using anticathelin-like antibodies; lanes 1 and 2, cathelin-like protein before and after digestion with enterokinase. (d) MALDI-TOF mass spectrometry. Molecular mass of pure human cathelin-like protein is single peak at 11167.5 Da. Internal standards were included and are seen as accompanying peaks.

DETAILED DESCRIPTION

Figure 1D:
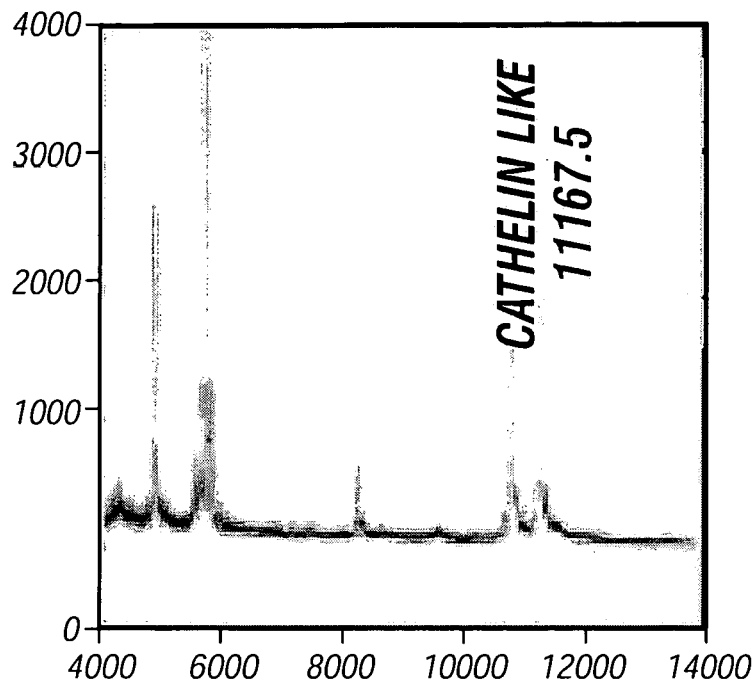

The present disclosure provides a novel class of cationic cathelin-like peptides and polypeptides that have antimicrobial activity. These peptides are useful for inhibiting microbial infection or growth. The peptides can be used, for example, as preservatives in foods or cosmetics, in topical lotions, creams, gels, ointments, as well as for parenteral administration, and the like. Many of the peptides of the disclosure are synergistic with conventional antibiotics and can be used as an adjunct therapy. In addition, such peptides are useful as antifungal agents, antitumor agents, and/or antiviral agents.

The disclosure demonstrates prokaryotic expression of recombinant full-length hCAP18 comprising LL-37 and its cathelin-like prosequence. The disclosure further demonstrates that the human cathelin-like domain acts as cysteine proteinase inhibitor and that it exhibits antibacterial activity against pathogens including *E. coli* and methicillin-resistant *Staphylococcus auaeus* (MRSA). This antimicrobial activity is distinct from that of the LL-37 peptide.

The antimicrobial activity of hCAP18/LL-37 has been attributed to the action of the C-terminal peptide (in humans known as LL-37) after proteolytic processing of the precursor protein (in humans known as hCAP18/LL-37) to "remove" the N-terminal cathelin-like domain.

Thus, the disclosure demonstrates that the cathelin-like domain of hCAP18 is a distinct contributor to skin innate host defense through inhibition of both bacterial growth and cysteine-proteinase-mediated tissue damage.

In humans, there are several classes of known AMPs including α-defensins, β-defensins, and cathelicidins. Cathelicidins are found in several mammalian species. Production of cathelicidins is induced in response to epithelial wounding or infectious challenge, or suppressed by the virulence mechanisms of certain bacterial pathogens, e.g., *Shigella dysenteriae*. Cathelicidin expression is also differentially effected in certain chronic inflammatory disorders. In psoriasis, cathelicidin levels are elevated and secondary infection is rare, whereas in atopic dermatitis cathelicidin expression is deficient and bacterial or viral superinfection is common. Therapeutic benefits of cathelicidin have been demonstrated experimentally, including decreased bacterial colonization of skin wounds following topical administration and improved pulmonary bacterial clearance with cathelicidin overexpression through viral gene transfer.

Cathelicidin proteins are composed of two distinct domains: an N-terminal "cathelin-like" or "prosequence" domain and the C-terminal domain of the mature AMP. The C-terminal domains of cathelicidins were among the earliest mammalian AMPs to show potent, rapid, and broad-spectrum killing activity. The term "cathelin-like" derives from the similarity of the N-terminal sequence with that of cathelin, a 12 kDa protein isolated from porcine neutrophils that shares similarity with the cystatin superfamily of cysteine protease inhibitors.

Cathelicidins are expressed in neutrophils and myeloid bone marrow cells and most epithelial sources, and were the first AMPs discovered in mammalian skin due to their presence in wound fluid. In the neutrophil, cathelicidins are synthesized as full-length precursor and targeted to the secondary granules where they are stored. Upon stimulation, the full-length cathelicidin protein is proteolytically processed to unleash the microbicidal activity of the C-terminal peptide from the cathelin-like domain.

The structure of the N-terminal 96–104 residue protein domain (the N-terminal cathelin-like domain) is believed to be stabilized by four cysteines engaged in two disulfide bonds. These four cysteines as wells their relative positions are well conserved in all species. The strict evolutionary conservation of this domain and its similarity to cystatins, a family of proteinase inhibitors, suggests it plays specific and independent biologic function in host defense.

The C-terminal 37 amino acids (LL-37) of the mature AMP of human cationic antibacterial protein of 18 kDa (hCAP18) has been characterized. LL-37 was originally referred to as FALL39, named for the first 4 N-terminal amino acids (phe-ala-leu-leu) of this domain and the total number of residues (i.e., 39). LL-37 is a peptide predicted to contain an amphipathic alpha helix and lacks cysteine, making it different from all other previously isolated human peptide antibiotics of the defensin family, each of which contain 3 disulfide bridges. Antibacterial peptides from different mammals contained a conserved pro-region very similar to cathelin. Full length hCAP18 comprises the cathelin-like precursor protein and the C-terminal LL-37 peptide, thus comprising 170 amino acids (SEQ ID NO:2).

The polypeptide comprising SEQ ID NO:2 has a number of distinct domains. For example, a signal domain comprising a sequence as set forth from about 1 to about $x_1$ of SEQ ID NO:2 is present, wherein $x_1$ is an amino acid between and inclusive of amino acids from about 29–31 of SEQ ID NO:2 (e.g., from about 1 to 30 of SEQ ID NO:2). The signal domain is typically cleaved following amino acid number 30 of SEQ ID NO:2, however, one of skill in the art will recognize that depending upon the enzyme used, the expression system used and/or the conditions under which proteolytic cleavage of the polypeptide takes place, the cleavage site may vary from 1 to 3 amino acid in either direction of amino acid number 30 of SEQ ID NO:2. Another domain comprises the N-terminal domain, comprising a cathelin-like peptide. The cathelin-like peptide comprises from about amino acid $x_2$ (wherein $x_2$ is between and inclusive of amino acids 29–31 of SEQ ID NO:2) to about amino acid $x_3$ (wherein $x_3$ is between and inclusive of amino acids 128–131 of SEQ ID NO:2). For example, the cathelin-like domain may comprise from about amino acid 31 to about amino acid number 131 of SEQ ID NO:2. Yet another domain of SEQ ID NO:2 comprises the C-terminal domain referred to as LL-37. The LL-37 domain comprises from about amino acid $x_4$ to amino acid 170 of SEQ ID NO:2, wherein $X_4$ is an amino acid residue between and inclusive of residues 128–134 of SEQ ID NO:2.

The complete hCAP18 gene is a compact gene of 1,963 bp with 4 exons. Exons 1–3 encode for a signal sequence and the cathelin region. Exon 4 contains the information for the mature antibacterial peptide, LL-37. Potential binding sites for acute-phase-response factors were identified in the promoter and in intron 2. The hCAP18 gene has been mapped to 3p21.3 by fluorescence in situ hybridization.

The full length hCAP18 gene product (SEQ ID NO:2) is cleaved by a serine protease to generate the antimicrobial peptide LL-37. The cleavage takes place after exocytosis, i.e., it occurs extracellularly.

The disclosure demonstrates prokaryotic expression of recombinant full-length hCAP18 comprising LL-37 and its cathelin-like prosequence. The disclosure further demonstrates that the human cathelin-like domain acts as cysteine proteinase inhibitor and that it exhibits antibacterial activity against pathogens including *E. coli* and methicillin-resistant *Staphylococcus auaeus* (MRSA). This antimicrobial activity is distinct from that of the LL-37 peptide.

Thus, the disclosure demonstrates that the cathelin-like domain of hCAP18 is a distinct contributor to skin innate host defense through inhibition of both bacterial growth and cysteine-proteinase-mediated tissue damage.

The term "antimicrobial" as used herein means that the peptide destroys, or inhibits or prevents the growth or proliferation of, a microbe (e.g., a bacterium, fungus, and/or virus). Likewise, the term "antiviral" as used herein means that a peptide destroys, or inhibits or prevents the growth or proliferation of a virus or a virus-infected cell. The term "anti-tumor" as used herein means that a peptide prevents, inhibits the growth of, or destroys, a tumor cell(s). Similarly, the term "antifungal" means that a peptide prevents, destroys, or inhibits the growth of a fungus.

As used herein, the term "cationic cathelin-like peptide" refers to a chain of amino acids that is about 96 to about 104 amino acids in length and comprises a sequence as set forth in SEQ ID NO:3 or the N-terminal cathelin-like domain of SEQ ID NO:2. A peptide is "cationic" if it has a pKa greater than 9.0. Typically, at least four of the amino acid residues of the cationic cathelin-like peptide are positively charged residues, e.g., lysine and arginine. "Positively charged" refers to the side chain of an amino acid residue that has a net positive charge at pH 7.0.

As is described below, a cationic cathelin-like peptide comprises an amino acid sequence represented by:

(Q/R)$X_1$(L/P)SY(K/R) (E/D)AVLRA(V/I)$X_2X_3X_4$N(E/Q)(Q/R)S(S/L) (D/E)$X_5$NLYRLLX$_6$L(D/N)$X_7X_8$PX$_9X_{10}$(D/E)$X_{11}$DPX$_{12}$(T/I) (P/R)K(P/S)V(S/R)F(T/R)VKETVC(P/G)(K/R)$X_{13}$(T/E)(Q/R)QX$_{14}$(P/L)EX$_{15}$CX$_{16}$FKX$_{17}X_{18}$G (L/R) VK(Q/R)CX$_{19}$G(A/T)V(T/I)L(D/N) $X_{20}X_{21}X_{22}X_{23}X_{24}$(F/L)D(I/L)(N/S)C(N/D) $X_{25}X_{26}X_{27}X_{28}X_{29}X_{30}X_{31}$ (SEQ ID NO:3)

wherein $X_1$ is A, V or T; $X_2$ is N, D or G; $X_3$ is G, R, D or Q; $X_4$ is L, I or F; $X_5$ is E, A or T; $X_6$ is Q, E or D; $X_7$ is S, Q or P; $X_8$ is Q, P, R or E or A; Xg is K, T, Q or N; $X_{10}$ is G, A, M or D; $X_{11}$ is G, E or V; $X_{12}$ is N, G or D; $X_{13}$ is P, T or A; $X_{14}$ is P, S or L; $X_{15}$ is Q, L, D or E; $X_{16}$ is G, D or A; $X_{17}$ is D, E or K; $X_{18}$ is N, D or Q; $X_{19}$ is E, V or M; $X_{20}$ is E, P or Q; $X_{21}$ is D, S or A; $X_{22}$ is T, I, R, A or N; $X_{23}$ is G, H or D; $X_{24}$ is S, Y or Q; $X_{25}$ is S, E or K; $X_{26}$ is I, D, A or L; $X_{27}$ is L, Q or N; $X_{28}$ is S, P, K or Q; $X_{29}$ is V, F or R; $X_{30}$ is R, F or K; and $X_{31}$ is F, A, R or K. In one embodiment, the cationic cathelin-like peptide comprises a sequence as set forth in SEQ ID NO:2 from about amino acid 31 to about amino acid 131.

The term "purified" as used herein refers to a peptide that is substantially free of other proteins, lipids, and polynucleotides (e.g., cellular components with which an in vivo-produced peptide would naturally be associated). Typically, the peptide is at least 70%, 80%, or most commonly 90% pure by weight.

Figure 5:
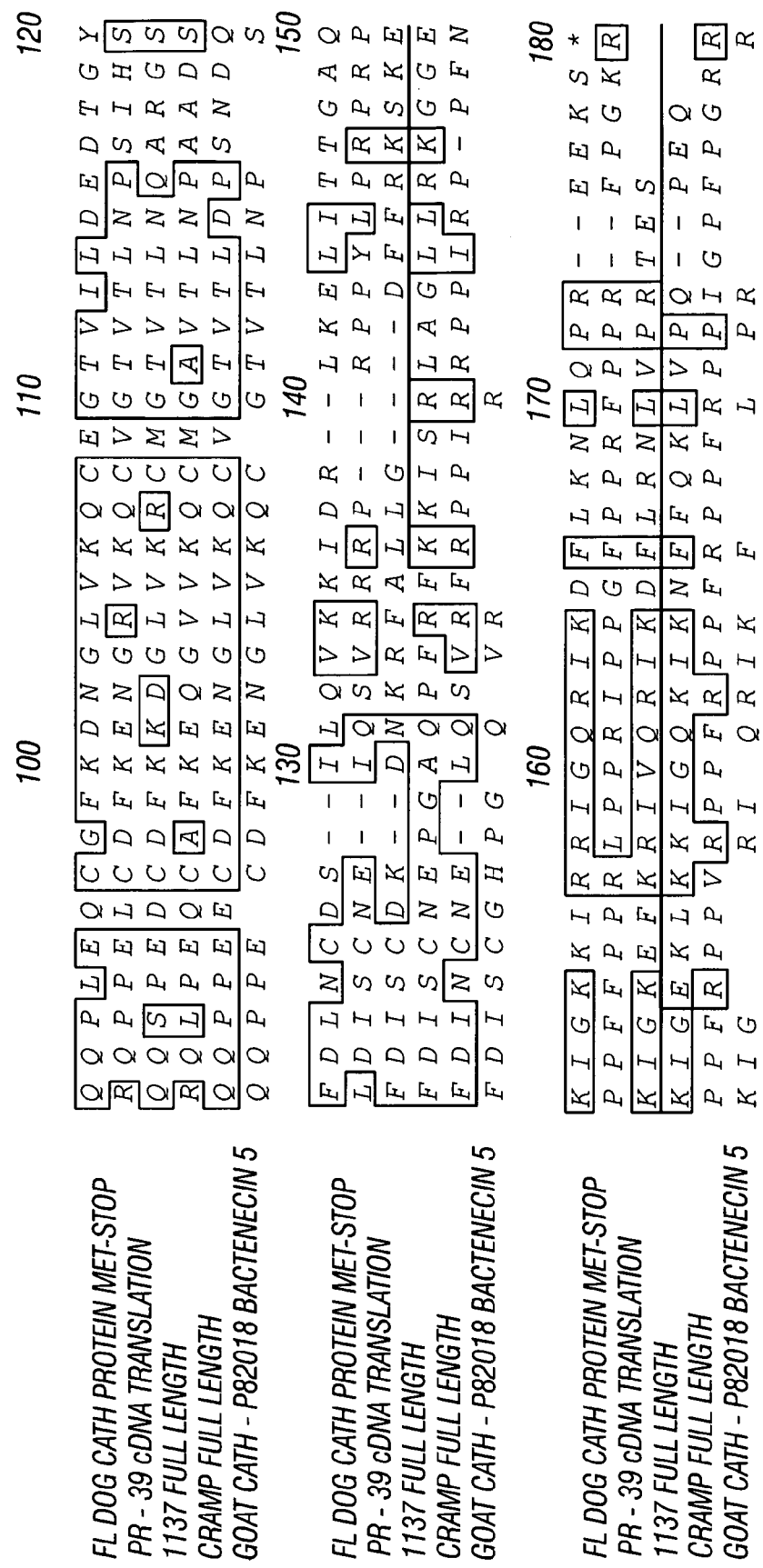
FIG. 5 shows a pile up of cathelicidin and related proteins and a consensus sequence (SEQ ID NOs:11–16, respectively).

The disclosure also includes analogs, derivatives, conservative variations, and cationic cathelin-like peptide variants of the enumerated cationic cathelin-like peptide, provided that the analog, derivative, conservative variation, or variant has a detectable antimicrobial activity. It is not necessary that the analog, derivative, variation, or variant have activity identical to the activity of the peptide from which the analog, derivative, conservative variation, or variant is derived. For example, using the alignment provided in FIG. 5, one of skill in the art can readily identify conserved amino acids and non-conserved amino acid. Using the alignment, one of skill in the art can readily identify which amino acid may be modified or substituted.

A cationic cathelin-like peptide "variant" is an antimicrobial peptide that is an altered form of a referenced antimicrobial cationic cathelin-like peptide. For example, the term "variant" includes an antimicrobial cationic cathelin-like peptide produced by the method disclosed herein in which at least one amino acid (e.g., from about 1 to 10 amino acids) of a reference peptide is substituted with another amino acid. The term "reference" peptide means any of the antimicrobial cationic cathelin-like peptides of the disclosure (e.g., as defined in the above formulas, e.g., SEQ ID NO: 2 and 3), from which a variant, derivative, analog, or conservative variation is derived. Included within the term "derivative" is a hybrid peptide that includes at least a portion of each of two antimicrobial cationic cathelin-like peptides (e.g., 30–80% of each of two antimicrobial cationic cathelin-like peptides). Derivatives can be produced by adding one or a few (e.g., 1–5) amino acids to an antimicrobial peptide without completely inhibiting the antimicrobial activity of the peptide. In addition, C-terminal derivatives, e.g., C-terminal methyl esters, can be produced and are encompassed by the disclosure.

The disclosure also includes peptides that are conservative variations of those peptides as exemplified herein. The term "conservative variation" as used herein denotes a polypeptide in which at least one amino acid is replaced by another, biologically similar residue. Examples of conservative variations include the substitution of one hydrophobic residue, such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acid, or glutamine for asparagine, and the like. Neutral hydrophilic amino acids that can be substituted for one another include asparagine, glutamine, serine and threonine. The term "conservative variation" also encompasses a peptide having a substituted amino acid in place of an unsubstituted parent amino acid; typically, antibodies raised to the substituted polypeptide also specifically bind the unsubstituted polypeptide.

Cationic cathelin-like peptide variants of the disclosure can be identified by screening a large collection, or library, of random peptides or peptides of interest using, for example, one of a number of animal models such as CRAMP knockout mice that display increased susceptability to skin infections. Cationic cathelin-like peptide variants can be, for example, a population of peptides related in amino acid sequence to SEQ ID NO:2 and 3 by having various substitutions based upon, for example, the sequence as set forth in SEQ ID NO:3.

Peptide libraries include, for example, tagged chemical libraries comprising peptides and peptidomimetic molecules. Peptide libraries also comprise those generated by phage display technology. Phage display technology includes the expression of peptide molecules on the surface of phage as well as other methodologies by which a protein ligand is or can be associated with the nucleic acid, which encodes it. Methods for the production of phage display libraries, including vectors and methods of diversifying the population of peptides, which are expressed, are known in the art (see, for example, Smith and Scott, Methods Enzymol. 217:228–257 (1993); Scott and Smith, Science 249: 386–390 (1990); and Huse, WO 91/07141 and WO 91/07149). These or other known methods can be used to produce a phage display library, from which the displayed peptides can be cleaved and assayed for antibacterial activity. If desired, a population of peptides can be assayed for activity, and an active population can be subdivided and the assay repeated in order to isolate an active peptide from the population. Other methods for producing peptides useful in the disclosure include, for example, rational design and mutagenesis based on the amino acid sequences of a cathelin-like peptide as set forth in SEQ ID NO:2 or 3, for example.

A cationic cathelin-like peptide variant can be a peptide mimetic, which is a non-amino acid chemical structure that mimics the structure of, for example, a cathelin-like peptide of SEQ ID NO:2 yet retains antimicrobial/antibacterial activity. Such a mimetic generally is characterized as exhibiting similar physical characteristics such as size, charge or hydrophobicity in the same spatial arrangement found in the cationic cathelin-like peptide counterpart. A specific example of a peptide mimetic is a compound in which the amide bond between one or more of the amino acids is replaced, for example, by a carbon—carbon bond or other bond well known in the art (see, for example, Sawyer, Peptide Based Drug Design, ACS, Washington (1995)).

The amino acids of a cationic cathelin-like peptide, cationic cathelin-like peptide variant or peptidomimetic of the disclosure are selected from the twenty naturally occurring amino acids, including, unless stated otherwise, L-amino acids and D-amino acids. The use of D-amino acids are particularly useful for increasing the life a a protein. Polypeptides incorporating D-amino acids are reistant to proteolytic digestion. The term amino acid also refers to compounds such as chemically modified amino acids including amino acid analogs, naturally occurring amino acids that are not usually incorporated into proteins such as norleucine, and chemically synthesized compounds having properties known in the art to be characteristic of an amino acid, provided that the compound can be substituted within a peptide such that it retains its biological activity. For example, glutamine can be an amino acid analog of asparagine, provided that it can be substituted within an active fragment of a cationic cathelin-like peptide, variant and the like such that it retains its antimicrobial/antibacterial activity. Other examples of amino acids and amino acids analogs are listed in Gross and Meienhofer, The Peptides: Analysis, Synthesis, Biology, Academic Press, Inc., New York (1983). An amino acid also can be an amino acid mimetic, which is a structure that exhibits substantially the same spatial arrangement of functional groups as an amino acid but does not necessarily have both the "-amino" and "-carboxyl" groups characteristic of an amino acid.

The activity of the peptides of the disclosure can be determined using conventional methods known to those of skill in the art, such as in a "minimal inhibitory concentration (MIC)", whereby the lowest concentration at which no change in OD is observed for a given period of time is recorded as the MIC. Alternatively, a "fractional inhibitory concentration (FIC)" assay can be used to measure synergy between the peptides of the disclosure, or the peptides in combination with known antibiotics. FICs can be performed by checkerboard titrations of peptides in one dimension of a microtiter plate, and of antibiotics in the other dimension, for example. The FIC is a function of the impact of one antibiotic on the MIC of the other and vice versa. A FIC of 1 indicates that the influence of the compounds is additive and a FIC of less than 1 indicates that the compounds act synergistically.

Peptides of the disclosure can be synthesized by commonly used methods such as those that include t-BOC or FMOC protection of alpha-amino groups. Both methods involve stepwise synthesis in which a single amino acid is added at each step starting from the C terminus of the peptide (See, Coligan, et al., *Current Protocols in Immunology*, Wiley Interscience, 1991, Unit 9). Peptides of the disclosure can also be synthesized by the well known solid phase peptide synthesis methods such as those described by Merrifield, J. Am. Chem. Soc., 85:2149, 1962) and Stewart and Young, Solid Phase Peptides Synthesis, Freeman, San Francisco, 1969, pp. 27–62) using a copoly(styrene-divinylbenzene) containing 0.1–1.0 mMol amines/g polymer. On completion of chemical synthesis, the peptides can be deprotected and cleaved from the polymer by treatment with liquid HF-10% anisole for about ¼–1 hours at 0° C. After evaporation of the reagents, the peptides are extracted from the polymer with a 1% acetic acid solution, which is then lyophilized to yield the crude material. The peptides can be purified by such techniques as gel filtration on Sephadex G-15 using 5% acetic acid as a solvent. Lyophilization of appropriate fractions of the column eluate yield homogeneous peptide, which can then be characterized by standard techniques such as amino acid analysis, thin layer chromatography, high performance liquid chromatography, ultraviolet absorption spectroscopy, molar rotation, or measuring solubility. If desired, the peptides can be quantitated by the solid phase Edman degradation.

The disclosure also includes isolated polynucleotides (e.g., DNA, cDNA, or RNA) encoding the peptides of the disclosure. Included are polynucleotides that encode analogs, mutants, conservative variations, and variants of the peptides described herein. The term "isolated" as used herein refers to a polynucleotide that is substantially free of proteins, lipids, and other polynucleotides with which an in vivo-produced polynucleotides naturally associated. Typically, the polynucleotide is at least 70%, 80%, or 90% isolated from other matter, and conventional methods for synthesizing polynucleotides in vitro can be used in lieu of in vivo methods. As used herein, "polynucleotide" refers to a polymer of deoxyribonucleotides or ribonucleotides, in the form of a separate fragment or as a component of a larger genetic construct (e.g., by operably linking a promoter to a polynucleotide encoding a peptide of the disclosure). Numerous genetic constructs (e.g., plasmids and other expression vectors) are known in the art and can be used to produce the peptides of the disclosure in cell-free systems or prokaryotic or eukaryotic (e.g., yeast, insect, or mammalian) cells. By taking into account the degeneracy of the genetic code, one of ordinary skill in the art can readily synthesize polynucleotides encoding the peptides of the disclosure. The polynucleotides of the disclosure can readily be used in conventional molecular biology methods to produce the peptides of the disclosure.

DNA encoding the cationic cathelin-like peptides of the disclosure can be inserted into an "expression vector." The term "expression vector" refers to a genetic construct such as a plasmid, virus or other vehicle known in the art that can be engineered to contain a polynucleotide encoding a polypeptide of the disclosure. Such expression vectors are typically plasmids that contain a promoter sequence that facilitates transcription of the inserted genetic sequence in a host cell. The expression vector typically contains an origin of replication, and a promoter, as well as genes that allow phenotypic selection of the transformed cells (e.g., an antibiotic resistance gene). Various promoters, including inducible and constitutive promoters, can be utilized in the disclosure. Typically, the expression vector contains a replicon site and control sequences that are derived from a species compatible with the host cell.

Transformation or transfection of a host cell with a polynucleotide of the disclosure can be carried out using conventional techniques well known to those skilled in the art. For example, where the host cell is *E. coli*, competent cells that are capable of DNA uptake can be prepared using the $CaCl_2$, $MgCl_2$ or RbCl methods known in the art. Alternatively, physical means, such as electroporation or microinjection can be used. Electroporation allows transfer of a polynucleotide into a cell by high voltage electric impulse. Additionally, polynucleotides can be introduced into host cells by protoplast fusion, using methods well known in the art. Suitable methods for transforming eukaryotic cells, such as electroporation and lipofection, also are known.

"Host cells" encompassed by of the disclosure are any cells in which the polynucleotides of the disclosure can be used to express the cationic cathelin-like peptides of the disclosure. The term also includes any progeny of a host cell. Host cells, which are useful, include bacterial cells, fungal cells (e.g., yeast cells), plant cells and animal cells. For example, host cells can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology (1986)). As representative examples of appropriate hosts, there may be mentioned: fungal cells, such as yeast; insect cells such as *Drosophila* S2 and *Spodoptera* Sf9; animal cells such as CHO, COS or Bowes melanoma; plant cells, and the like. The selection of an appropriate host is deemed to be within the scope of those skilled in the art from the teachings herein.

Host cells can be eukaryotic host cells (e.g., mammalian cells). In one aspect, the host cells are mammalian production cells adapted to grow in cell culture. Examples of such cells commonly used in the industry are CHO, VERO, BHK, HeLa, CV1 (including Cos; Cos-7), MDCK, 293, 3T3, C127, myeloma cell lines (especially murine), PC12 and W138 cells. Chinese hamster ovary (CHO) cells are widely used for the production of several complex recombinant proteins, e.g. cytokines, clotting factors, and antibodies (Brasel et al., Blood 88:2004–2012 (1996); Kaufman et al., J. Biol Chem 263: 6352–6362 (1988); McKinnon et al., J Mol Endocrinol 6:231–239 (1991); Wood et al., J. Immunol 145:3011–3016 (1990)). The dihydrofolate reductase (DHFR)-deficient mutant cell lines (Urlaub et al., Proc Natl Acad Sci USA 77:4216–4220 (1980)) are the CHO host cell lines commonly used because the efficient DHFR selectable and amplifiable gene expression system allows high level recombinant protein expression in these cells (Kaufman, Meth Enzymol 185:527–566 (1990)). In addition, these cells are easy to manipulate as adherent or suspension cultures and exhibit relatively good genetic stability. CHO cells and recombinant proteins expressed in them have been extensively characterized and have been approved for use in clinical manufacturing by regulatory agencies.

Polynucleotides encoding the peptides of the disclosure can be isolated from a cell (e.g., a cultured cell), or they can be produced in vitro. A DNA sequence encoding a cationic cathelin-like peptide of interest can be obtained by: 1) isolation of a double-stranded DNA sequence from genomic DNA; 2) chemical manufacture of a polynucleotide such that it encodes the cationic cathelin-like peptide of interest; or 3) in vitro synthesis of a double-stranded DNA sequence by reverse transcription of mRNA isolated from a donor cell (i.e., to produce cDNA). Among the standard procedures for isolating cDNA sequences of interest is the formation of plasmid or phage containing cDNA libraries that are derived from reverse transcription of mRNA in donor cells that have a high level of genetic expression. When used in combination with polymerase chain reaction technology, even rare gene products can be cloned.

The disclosure also includes isolated polynucleotides (e.g., DNA, cDNA, or RNA) encoding the peptides of the disclosure. Included are polynucleotides that encode analogs, mutants, conservative variations, and variants of the peptides described herein. For example, an isolated polynucleotide encoding a cationic cathelin-like peptide of the disclosure can comprise the sequence of SEQ ID NO:1. In one aspect, a polynucleotide encoding a cationic cathelin-like peptide comprises SEQ ID NO:1 from about nucleotide 91 to about nucleotide 390.

In one embodiment, the disclosure provides an isolated polynucleotide sequence encoding a cationic cathelin-like peptide or variant thereof. An exemplary cationic cathelin-like peptide of the disclosure has an amino acid sequence as set forth in SEQ ID NO:3. A specific exemplary cationic cathelin-like peptide of the disclosure comprises the N-terminal amino acid sequence as set forth in SEQ ID NO:2 from about amino acid 31 to about 131. Polynucleotide sequences encoding a peptide of SEQ ID NO:3 or variants thereof, or SEQ ID NO:2 from about amino acid 31 to amino acid 131 or variants thereof include DNA, cDNA and RNA sequences. Such polynucleotides include naturally occurring, synthetic, and intentionally manipulated polynucleotides. For example, a cationic cathelin-like peptide or variant polynucleotide may be subjected to site-directed mutagenesis. A cationic cathelin-like peptide or variant polynucleotide includes sequences that are degenerate as a result of the genetic code. There are 20 natural amino acids, most of which are specified by more than one codon. Therefore, all degenerate nucleotide sequences are included so long as the amino acid sequence of a cationic cathelin-like peptide or variant encoded by the nucleotide sequence is functionally unchanged. Accordingly, a polynucleotide of the disclosure includes (i) a polynucleotide encoding a cationic cathelin-like peptide or variant; (ii) a polynucleotide encoding SEQ ID NO:2 or a variant thereof, or SEQ ID NO:3 or a variant thereof; (iii) a polynucleotide comprising SEQ ID NO:1 or SEQ ID NO:1 from about nucleotide 91 to about nucleotide 390; (iv) a polynucleotide of (iii), wherein T is U; and (v) a polynucleotide comprising a sequence that is complementary to (iii) and (iv) above. A "polynucleotide" of the disclosure also includes those polynucleotides capable of hybridizing, under stringent hybridization conditions, to sequences of (iii)–(v), above. "Stringent hybridization conditions" refers to an overnight incubation at 42° C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C. It will be recognized that a polynucleotide of the disclosure, may be operably linked to a second heterologous polynucleotide such as a promoter or a heterologous sequence encoding a desired peptide or polypeptide sequence.

Any of various art-known methods for protein purification can be used to isolate the peptides of the disclosure. For example, preparative chromatographic separations and immunological separations (such as those employing monoclonal or polyclonal antibodies) can be used. Carrier peptides can facilitate isolation of fusion proteins that include the peptides of the disclosure. Purification tags can be operably linked to a cationic cathelin-like peptide of the disclosure. For example, glutathione-S-transferase (GST) allows purification with a glutathione agarose affinity column. When either Protein A or the ZZ domain from *Staphylococcus aureus* is used as the tag, purification can be accomplished in a single step using an IgG-sepharose affinity column. The pOprF-peptide, which is the N-terminal half of the *P. aeruginosa* outer membrane protein F, can readily be purified because it is the prominent protein species in outer membrane preparations. If desired, the fusion peptides can be purified using reagents that are specifically reactive with (e.g., specifically bind) the cationic cathelin-like peptide of the fusion peptide. For example, monoclonal or polyclonal antibodies that specifically bind the cationic cathelin-like peptide can be used in conventional purification methods. Techniques for producing such antibodies are well known in the art.

A fusion construct comprising a polypeptide linked to a cationic cathelin-like peptide of the disclosure can be linked at either the amino or carboxy terminus of the peptide. Typically, the polypeptide that is linked to the cationic cathelin-like peptide is sufficiently anionic such that the positive charge associated with the cationic cathelin-like peptide is overcome and the resulting fusion peptide has a net charge that is neutral or negative. The anionic polypeptide can correspond in sequence to a naturally-occurring protein or can be entirely artificial in design. Functionally, the polypeptide linked to a cationic cathelin-like peptide (the "carrier polypeptide") may help stabilize the cationic cathelin-like peptide and protect it from proteases, although the carrier polypeptide need not be shown to serve such a purpose. Similarly, the carrier polypeptide may facilitate transport of the fusion peptide. Examples of carrier polypeptides that can be utilized include anionic pre-pro peptides and anionic outer membrane peptides. Examples of carrier polypeptides include glutathione-S-transferase (GST), protein A of *Staphylococcus aureus*, two synthetic IgG-binding domains (ZZ) of protein A, outer membrane protein F of *Pseudomonas aeruginosa*, and the like. The disclosure is not limited to the use of these polypeptides; others suitable carrier polypeptides are known to those skilled in the art. In another aspect, a linker moiety comprising a protease cleavage site may be operably linked to a cationic antiviral peptide or variant of the disclosure. For example, the linker may be operable between to domains of a fusion protein (e.g., a fusion protein comprising a cationic cathelin-like peptide and a carrier polypeptide). Because protease cleavage recognition sequences generally are only a few amino acids in length, the linker moiety can include the recognition sequence within flexible spacer amino acid sequences, such as GGGGS (SEQ ID NO:4). For example, a linker moiety including a cleavage recognition sequence for Adenovirus endopeptidase could have the sequence GGGGGGSMFG GAKKRSGGGG GG (SEQ ID NO:5). If desired, the spacer DNA sequence can encode a protein recognition site for cleavage of the carrier polypeptide from the cationic cathelin-like peptide. Examples of such spacer DNA sequences include, but are not limited to, protease cleavage sequences, such as that for Factor Xa protease, the methionine, tryptophan and glutamic acid codon sequences, and the pre-pro defensin sequence. Factor Xa is used for proteolytic cleavage at the Factor Xa protease cleavage sequence, while chemical cleavage by cyanogen bromide treatment releases the peptide at the methionine or related codons. In addition, the fused product can be cleaved by insertion of a codon for tryptophan (cleavable by o-iodosobenzoic acid) or glutamic acid (cleavable by *Staphylococcus* protease). Insertion of such spacer DNA sequences is not a requirement for the production of functional cationic cathelin-like peptides, such sequences can enhance the stability of the fusion peptide. The pre-pro defensin sequence is negatively charged; accordingly, it is envisioned within the disclosure that other DNA sequences encoding negatively charged peptides also can be used as spacer DNA sequences to stabilize the fusion peptide.

The disclosure also provides a method for inhibiting the growth of a bacterium by contacting the bacterium with an inhibiting effective amount of a peptide of the disclosure. The term "contacting" refers to exposing the bacterium to the peptide so that the peptide can inhibit, kill, or lyse bacteria. Contacting of an organism with a cationic cathelin-like peptide of the disclosure can occur in vitro, for example, by adding the peptide to a bacterial culture to test for susceptibility of the bacteria to the peptide, or contacting a bacterially contaminated surface with the peptide. Alternatively, contacting can occur in vivo, for example by administering the peptide to a subject afflicted with a bacterial infection or susceptible to infection. In vivo contacting includes both parenteral as well as topical. "Inhibiting" or "inhibiting effective amount" refers to the amount of peptide that is sufficient to cause, for example, a bacteriostatic or bactericidal effect. Bacteria that can be affected by the peptides of the disclosure include both gram-negative and gram-positive bacteria. For example, bacteria that can be affected include *Staphylococcus aureus, Streptococcus pyogenes* (group A), *Streptococcus* sp. (viridans group), *Streptococcus agalactiae* (group B), *S. bovis, Streptococcus* (anaerobic species), *Streptococcus pneumoniae*, and *Enterococcus* sp.; Gram-negative cocci such as, for example, *Neisseria gonorrhoeae, Neisseria meningitidis*, and Branhamella catarrhalis; Gram-positive bacilli such as *Bacillus anthracis, Bacillus subtilis*, P.acne *Corynebacterium diphtheriae* and *Corynebacterium* species which are diptheroids (aerobic and anerobic), *Listeria monocytogenes, Clostridium tetani, Clostridium difficile, Escherichia coli, Enterobacter* species, *Proteus mirabilis* and other sp., *Pseudomonas aeruginosa, Klebsiella pneumoniae, Salmonella, Shigella, Serratia*, and *Campylobacter jejuni*. Infection with one or more of these bacteria can result in diseases such as bacteremia, pneumonia, meningitis, osteomyelitis, endocarditis, sinusitis, arthritis, urinary tract infections, tetanus, gangrene, colitis, acute gastroenteritis, impetigo, acne, acne posacue, wound infections, born infections, fascitis, bronchitis, and a variety of abscesses, nosocomial infections, and opportunistic infections. Fungal organisms may also be affected by the cationic cathelin-like peptides of the disclosure and include dermatophytes (e.g., *Microsporum canis* and other *Microsporum* sp.; and *Trichophyton* sp. such as *T. rubrum*, and *T. mentagrophytes*), yeasts (e.g., *Candida albicans, C. Tropicalis*, or other *Candida* species), *Saccharomyces cerevisiae, Torulopsis glabrata, Epidermophyton floccosum, Malassezia furfur* (*Pityropsporon orbiculare*, or *P. ovale*), *Cryptococcus neoformans, Aspergillus fumigatus, Aspergillus nidulans*, and other *Aspergillus* sp., *Zygomycetes* (e.g., *Rhizopus, Mucor*), *Paracoccidioides brasiliensis, Blastomyces dermatitides, Histoplasma capsulatum, Coccidioides immitis*, and *Sporothrix schenckii*. The method for inhibiting the growth of bacteria can also include contacting the bacterium with the peptide in combination with one or more antibiotics.

A peptide(s) of the disclosure can be administered to any host, including a human or non-human animal, in an amount effective to inhibit growth of a bacterium, virus, or fungus. Thus, the peptides are useful as antimicrobial agents, antiviral agents, and/or antifungal agents.

Any of a variety of art-known methods can be used to administer the peptide to a subject. For example, the peptide of the disclosure can be administered parenterally by injection or by gradual infusion over time. The peptide can be administered intravenously, intraperitoneally, intramuscularly, subcutaneously, intracavity, or transdermally. In another aspect, a cationic cathelin-like peptide of the disclosure may be formulated for topical administration (e.g., as a lotion, cream, spray, gel, or ointment). Examples of formulations in the market place include topical lotions, creams, soaps, wipes, and the like. It may be formulated into liposomes to reduce toxicity or increase bioavailability. Other methods for delivery of the peptide include oral methods that entail encapsulation of the peptide in microspheres or proteinoids, aerosol delivery (e.g., to the lungs), or transdermal delivery (e.g., by iontophoresis or transdermal electroporation). Other methods of administration will be known to those skilled in the art.

Preparations for parenteral administration of a peptide of the disclosure include sterile aqueous or non-aqueous solutions, suspensions, and emulsions. Examples of non-aqueous solvents are propylene glycol, polyethylene glycol, vegetable oils (e.g., olive oil), and injectable organic esters such as ethyl oleate. Examples of aqueous carriers include water, saline, and buffered media, alcoholic/aqueous solutions, and emulsions or suspensions. Examples of parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives such as, other antimicrobial, anti-oxidants, cheating agents, inert gases and the like also can be included.

The disclosure provides a method for inhibiting a topical bacterial or fungal-associated disorder by contacting or administering a therapeutically effective amount of a peptide of the disclosure to a subject who has, or is at risk of having, such a disorder. The term "inhibiting" means preventing or ameliorating a sign or symptoms of a disorder (e.g., a rash, sore, and the like). Examples of disease signs that can be ameliorated include an increase in a subject's blood level of TNF, fever, hypotension, neutropenia, leukopenia, thrombocytopenia, disseminated intravascular coagulation, adult respiratory distress syndrome, shock, and organ failure. Examples of subjects who can be treated in the disclosure include those at risk for, or those suffering from, a toxemia, such as endotoxemia resulting from a gram-negative bacterial infection, venom poisoning, or hepatic failure. Other examples include subjects having a dermatitis as well as those having skin infections or injuries subject to infection with gram-positive or gram-negative bacteria or a fungus. Examples of candidate patients include those suffering from infection by *E. coli, Hemophilus influenza B, Neisseria meningitides, staphylococci,* or *pneumococci*. Other patients include those suffering from gunshot wounds, renal or hepatic failure, trauma, burns, immunocompromising infections (e.g., HIV infections), hematopoietic neoplasias, multiple myeloma, Castleman's disease or cardiac myxoma. Those skilled in the art of medicine can readily employ conventional criteria to identify appropriate subjects for treatment in accordance with the disclosure.

The term "therapeutically effective amount" as used herein for treatment of a subject afflicted with a disease or disorder means an amount of cationic cathelin-like peptide sufficient to ameliorate a sign or symptom of the disease or disorder. For example, a therapeutically effective amount can be measured as the amount sufficient to decrease a subject's symptoms of dermatitis or rash by measuring the frequency of severity of skin sores. Typically, the subject is treated with an amount of cationic cathelin-like peptide sufficient to reduce a symptom of a disease or disorder by at least 50%, 90% or 100%. Generally, the optimal dosage of the peptide will depend upon the disorder and factors such as the weight of the patient, the type of bacteria or fungal infection, the weight, sex, and degree of symptoms. Nonetheless, suitable dosages can readily be determined by one skilled in the art. Typically, a suitable dosage is 0.5 to 40 mg peptide/kg body weight, e.g., 1 to 8 mg peptide/kg body weight.

If desired, a suitable therapy regime can combine administration of a peptide(s) of the disclosure with one or more additional therapeutic agents (e.g., an inhibitor of TNF, an antibiotic, and the like). The peptide(s), other therapeutic agents, and/or antibiotic(s) can be administered, simultaneously, but may also be administered sequentially. Suitable antibiotics include aminoglycosides (e.g., gentamicin), beta-lactams (e.g., penicillins and cephalosporins), quinolones (e.g., ciprofloxacin), and novobiocin. In addition, the C-terminal fragment of SEQ ID NO:2 comprising LL-37 has antibacterial activity. Accordingly, a combination of the N-terminal fragment of SEQ ID NO:2 comprising the cathelin-like domain (e.g., SEQ ID NO:2 from about amino acid 31 to amino acid 131) and the C-terminal domain comprising LL-37 (e.g., amino acids 132 to 170) can be co-administered or administered sequentially. Generally, the antibiotic is administered in a bactericidal amount. However, the peptide provides for a method of increasing antibiotic activity by permeabilizing the bacterial outer membrane and combinations involving peptide and a sub-inhibitory amount (an amount lower than the bactericidal amount) of antibiotic can be administered. Typically, the cationic cathelin-like peptide and antibiotic are administered within 48 hours of each other (e.g., 2–8 hours, or may be administered simultaneously). A "bactericidal amount" is an amount sufficient to achieve a bacteria-killing blood concentration in the subject receiving the treatment. In accordance with its conventional definition, an "antibiotic," as used herein, is a chemical substance that, in dilute solutions, inhibits the growth of, or kills microorganisms. Also encompassed by this term are synthetic antibiotics (e.g., analogs) known in the art.

The peptides of the disclosure can be used, for example, as preservatives or sterilants of materials susceptible to microbial or viral contamination. For example, the peptides can be used as preservatives in processed foods (e.g., to inhibit organisms such as *Salmonella, Yersinia,* and *Shigella*). If desired, the peptides can be used in combination with antibacterial food additives, such as lysozymes. The peptides of the disclosure also can be used as a topical agent, for example, to inhibit *Pseudomonas* or *Streptococcus* or kill odor-producing microbes (e.g., *Micrococci*). The optimal amount of a cationic cathelin-like peptide of the disclosure for any given application can be readily determined by one of skill in the art.

The cationic cathelin-like peptides of the disclosure are also useful in promoting would repair and tissue regeneration. Matrix metalloproteinases (MMPS) are inflammatory enzymes that degrade proteins in various tissues. Recent scientific research has shown elevated levels of proteases (e.g., MMPs) in chronic wound exudate, the fluid that bathes the wound bed. These excess proteases cause degradation of important extracellular matrix proteins and inactivation of vital growth factors that are essential in the wound healing process. This may contribute to a sub-optimal healing environment resulting in delayed wound healing.

The cationic cathelin-like peptides of the disclosure can be used to treat damaged tissue, such as wounds (in particular chronic wounds), more effectively. As demonstrated herein, the cationic cathelin-like peptides of the disclosure are effective protease inhibitors. The cationic cathelin-like peptides of the disclosure are capable of inhibiting the action of specific proteins that are upregulated in a wound environment wherein those proteins have an adverse effect in the wound environment. Typically the adverse effect is a deleterious effect on wound healing. Hence, the cationic cathelin-like peptides of the disclosure can be used to inhibit the deleterious effects of proteases that are upregulated in a wound environment. Simultaneously, the cationic cathelin-like peptides of the disclosure also are capable of serving as antibacterial agents that reduce the risk of infection at a wound site by inhibiting proteases produced by pathogens in the wound site.

Studies have reported that the lysosomal cysteine proteinase cathepsin L is present in inflammatory cells, and may contribute substantially to tissue injury at inflammatory lesions due to its potent elastinolytic and collagenolytic activities. Recombinant human cathelin-like protein was able to inhibit the proteolytic activity of the human cysteine proteinase cathepsin L. Accordingly, the administration of cationic cathelin-like peptide can mitigate tissue injury and other potentially deleterious effects of cathepsin L, and potentially other proteinases, released from lysosomes during inflammatory responses. Moreover, several human pathogens secrete cysteine proteases that have been shown to play a role in disease pathogenesis, including SpeB and IdeS of *Streptococcus pyogenes*, Lys-gingipain of *Porphyromonas gingivalis*, and the extracellular cysteine proteases Ehcp1-6 of *Entamoeba histolytica*. Theoretically, the inhibition of such microbial virulence determinants may be another adaptive function of the cathelin-like domain in innate immune defense.

Typically the cationic cathelin-like peptide of the disclosure does not have an activity profile over a broad range of proteases. Instead, the cationic cathelin-like peptide is capable of acting on certain adverse proteins (e.g. a specific protease) that is upregulated in a damaged tissue. In some circumstances, the cationic cathelin-like peptide may act on a few proteins that are upregulated in a damaged tissue. Typically, the cationic cathelin-like peptide limits the specific proteolytic degradation effect(s) of at least one adverse protease that has a deleterious effect on wound healing. For example, the cationic cathelin-like peptides of the disclosure can be used to inhibit various cysteine proteases in a wound. Those of skill in the art will also recognize that various pathogenic organisms utilize cysteine protease to modulate their environment including infectivity and tissue destruction. Accordingly, the cationic cathelin-like peptides of the disclosure can be used to treat wounds and infection by inhibiting cysteine protease activity.

The following examples are intended to illustrate but not limit the disclosure. While they are typical of those that might be used, other procedures known to those skilled in the art may alternatively be used.

EXAMPLES

Construction of human cathelicidin expression vectors. Expression plasmids containing the human full-length cathelicidin cDNA (hCAP18/LL-37) residues (31–170) or the cathelin-like domain residues (31–131) were constructed as fusion proteins in the pET-28 vector (Novagen, Madison, Wis.) using standard methods (Sambrook et al., 1989). High-fidelity polymerase chain reaction was used to amplify the coding sequence of hCAP18/LL-37 with primers designed from the published sequence: forward primer P1, 5'-TCCGAGCTCGACGATG-ACGATAAGCTGCTGGGT-GATTTCTTCCGG-3' (SEQ ID NO:6), containing SacI recognition site and enterokinase cleavage site, and reverse primer P2, 5'-CCGCTCGAGCTAGGACTCTGTCCTGGG-TACAAGATTCCG-3' (SEQ ID NO:7). For plasmid pET-Cath, primer P1 (above) and reverse primer P3, 5'-CCGCTCGAGCTACTAGGCAAAT CTCTTGTTATC-CTT-3' (SEQ ID NO:8) were used. P2 and P3 both contain stop codons and XhoI restriction site extensions. SacI and XhoI digested polymerase chain reaction amplicons were used for unidirectional ligation into pET-28 vector. The pET-hCAP18 and pET-Cath constructs were confirmed by plasmid purification and direct DNA sequencing.

Expression of cathelicidin proteins. pET-hCAP18 or pET-Cath were transformed into protease-deficient E. coli strain BL21 (DE3). Overnight cultures of each in Luria-Bertani broth (LB) (1% bactotryptone, 0.5% yeast extract, 1% NaCl) supplemented with kanamycin (50 mg per ml) were used to inoculate 1 L LB broth and then grown at 37° C. with agitation to 0.6 OD at 600 nm. Expression was induced by addition of isopropyl-beta-D-thiogalactopyranoside (IPTG) to concentration of 0.5 mM. Cells were harvested by centrifugation (6500×g) for 10 min at 41° C. and then resuspended in 50 ml ice-cold sonication buffer (0.1 M Tris-HCl pH 8.0; 0.01 M $Na_2HPO_4$, 0.1 M NaCl; 0.05 M ethylene-diamine tetraacetic acid (EDTA); 0.005 M beta-mercaptoethanol) supplemented with the protease inhibitors 0.1% aprotinin and 2 mM phenylmethylsulfonyl fluoride. Cells were disrupted by sonication on ice and the mixture was centrifuged at 20,000×g for 30 min to separate the insoluble material. Recombinant protein solubility was assessed by comparative sodium dodecyl sulfate polyacrylamide gel electrophoresis (SDS-PAGE) separation of both the supernatant and the pellet fractions. The supernatant fraction containing soluble recombinant proteins was collected and guanidine-HCl and beta-mercaptoethanol were added to final concentrations of 6 M and 0.1%, respectively. The pellet resulting from the centrifugation was washed with 50 mM Tris-HCl and 5 mM EDTA. Insoluble full-length hCAP18/LL-37 and cathelin-like proteins were extracted overnight at 41° C. with lysis buffer supplemented with 6 M guanidine-HCl and beta-mercaptoethanol with yield of 70%–90% without degradation. The suspension was then centrifuged at 20,000×g for 30 min to remove the remaining insoluble material. The supernatants of both extractions were dialyzed against 200 mM NaCl, 200 mM L-arginine, 10 mM beta-mercaptoethanol, and 50 mM Tris-HCl pH 8.0, followed by extensive dialysis against 10 mM Tris-HCl pH 7.5. The solution was centrifuged for 10 min at 15,000×g to remove any precipitate. Proteins were pooled with the soluble fractions obtained earlier.

Purification of recombinant proteins was performed using immobilized metal ion chromatography. The supernatant was dialyzed against buffer A consisting of 0.5 M NaCl, 0.02 M $Na_2HPO_4$ pH 7.5. Proteins were loaded onto an $Ni^{2+}$-NTA 5 ml His-Trap column (Pharmacia Biotech, Piscataway, N.J.) previously equilibrated with buffer A to which 40 mM imidazole was added (flow rate 1 ml per min). The column was washed with 50 volumes of buffer A containing 40 mM imidazole to remove non-specific bound materials and bound proteins were eluted with 500 mM imidazole in buffer A, collecting 1 ml fractions. The elution profile was monitored by separation of samples by SDS-PAGE. Fractions containing proteins of interest were pooled and dialyzed against 0.5 M NaCl, 0.02 M $Na_2HPO_4$ pH 7.5 and the purification step was repeated at least twice. Eluted fractions were pooled and were dialyzed against enterokinase buffer (50 mM Tris-HCl pH 8.0, 1 mM $CaCl_2$, 0.1% Tween-20).

Enterokinase digestion. The upstream 43-residue N-terminal fusion sequence of pET containing the enterokinase recognition sequence DDDDK (SEQ ID NO:9) was cleaved from the recombinant hCAP18/LL-37 and Cath proteins by digestion with enterokinase (obtained as 1 unit per ml solution from Invitrogen, Carlsbad, Calif.). The reaction was incubated at 37° C. overnight with an enzyme:protein substrate ratio of 1:25. Digested proteins were dialyzed against 10 mM Tris-HCl pH 7.5.

SDS-PAGE and immunoblotting. The purity of cathelin-like or hCAP18/LL-37 protein was first confirmed by SDS-PAGE followed by Coomassie blue and silver staining. For Western blot, protein was separated by SDS-PAGE and was then transferred to nitrocellulose membranes using the Bio-Rad system. Membranes were blocked for 1 h at room temperature with 0.1% low fat milk in 50 mM Tris-HCl, pH 7.5, 150 mM NaCl, 0.2% Tween-20, and were probed overnight at 41° C. with chicken polyclonal anticathelin-like antibodies (1:15,000) to detect cathelin-like protein or with rabbit anti-LL-37 antibodies (1:6000) to detect full-length hCAP18/LL-37, followed by extensive washing. Immunoreactive materials were detected by enhanced chemiluminescence using horseradish peroxidase conjugated antichicken antibodies (1:20,000) or horseradish peroxidase conjugated antirabbit antibodies (1:5000).

Matrix-assisted laser desorption/ionization time of flight (MALDI-TOF) mass spectrometry. A MALDI-TOF mass spectrometer (Applied Biosystems, Framingham, Mass.) was used to analyze purified proteins and further confirm identity and purity. Protein samples were prepared for analysis by mixing in 1:1 ratio with sinapinic acid matrix (3,5-dimethoxy-4-hydroxycinnamic acid). Calibration was performed using internal standards: bovine insulin, apomyoglobin, and thioredoxin (Core facility at the University of California, San Diego).

Proteinase activity inhibition assay. Proteinase inhibitory activity of recombinant cathelin-like protein was assayed spectrofluorometrically by measuring its inhibitory action against human liver cathepsin L (Calbiochem, Calif.). For the reaction assay, cathepsin L (0.1 mU) in the assay buffer (340 nM sodium acetate, 60 mM acetic acid, 8 mM dithiothreitol, and 4 mM EDTA, pH 5.5, supplemented with 0.1% BRIJ 35) was preincubated for 2 min at 30° C. with $10^{-6}$ M cathelin-like protein before adding 20 mM of substrate Z-Phe-Arg-7-amido-4-methylcoumarin (Calbiochem). When hydrolyzed by cathepsin L, this substrate releases highly fluorescent 7-amido-4-methylcoumarin (AMC). AMC intensity was determined using spectrophotometer at 370 nm excitation and an emission wavelength of 460 nm. One unit was defined as the amount of enzyme that will hydrolyze 1.0 mmol of Z-Phe-Arg-AMC per min at 25° C., pH 5.5.

Antimicrobial assays. *E. coli* (ATCC 25922), *Pseudomonas aeruginosa* (ATCC 8427), *Salmonella typhimurium* (ATCC 13311), *Proteus vulgaris* (ATCC 8427), *Staphylococcus epidermidis* (ATCC 12228), and MRSA (ATCC 33591) isolates were maintained on trypticase soy broth (TSB) agar plates. Individual colonies were selected and cultured overnight in TSB, subcultured once at 1:50 in fresh TSB, and then grown to stationary phase for use in all experiments. The radial diffusion assay was performed in 0.5% agarose and 0.75% tryptone brought to ebullition and cooled to 43° C., and then mixed with 100 ml of bacterial suspension and poured into a 10 cm Petri dish. A series of small wells (diameter, 3 mm) were punched in the plate after the agarose solidified. Two microliters of test samples were applied in each well. Plates were incubated at 37° C. overnight to allow visible growth of bacteria. Antibacterial activity was indicated by the clear zone (no bacterial growth) around the well.

The colony-forming assay (CFU) was performed. Bacterial cultures (*E. coli* or MRSA) were collected at the logarithmic phase of growth in TSB, washed twice with phosphate-buffered saline, pH 7.4, and diluted to 104 CFU per ml in 10 mM phosphate buffer, pH 7.4, $Na_2HPO_4$/$NaH_2PO_4$-1% TSB (g per 1). Forty-five microliters of bacterial suspension were mixed with 5 ml of $H_2O$ (control) or with 5 ml of different concentrations of cathelin-like proteins, and the mixture was incubated at 37° C. Every 30 min, a 10 ml aliquot of the reaction mixture was plated directly onto a TSB agar plate and then incubated at 37° C. overnight for enumeration of CFU. Data are reported as growth index=final CFU/CFU in initial inoculum.

Processing of full-length hCAP18/LL-37 to cathelin-like protein and LL-37. Full-length hCAP18/LL-37 recombinant protein (10 ng) was incubated with 10 mU of human neutrophil elastase (Calbiochem) at 37° C. for 30 min. The sample was subsequently boiled in Laemmli sample buffer and run by SDS-PAGE followed by immunoblot analysis with anticathelin-like and anti-LL37 antibodies.

Expression and purification of cathelicidin proteins in *E. coli*. In order to achieve efficient expression of these proteins in *E. coli*, cDNA encoding full-length hCAP18/LL-37 or cathelin-like domain alone were cloned into the pET 28a(+) expression vector system (FIG. 1a). This system generates fusion proteins with an N-terminal peptide of 5 kDa containing a His(6) purification tag. Through primer design, a sequence corresponding to an enterokinase cleavage site, pentapeptide $(Asp)_4$-Lys, was inserted after the fusion domain and before the cDNA of interest. Cultures of BL21 (DE3) bacteria transformed with either pET-hCAP18 or pET-Cath were then used for expression following IPTG induction. Over 70% of recombinant cathelin-like proteins were found in the soluble fraction. Only about 40% of full-length cathelicidin proteins were soluble, however. The other fraction was found in the insoluble form. The expression of cathelicidin proteins with His-tag sequence at their N-terminus allowed for convenient purification from other soluble bacterial proteins using immobilized metal affinity chromatography. Proteins were further purified to homogeneity using size exclusion chromatography. The purity of recombinant cathelin-like protein after elution was first checked by SDS-PAGE (FIG. 1b). A band of approximately 16 kDa, which corresponds to the cathelin-like region and the fusion sequence (5 kDa), was detected by Coomassie blue staining (FIG. 1b). The identity of the bands of expected size was confirmed by Western blot using antibodies against the cathelin-like domain (FIG. 1c). A single band of approximately 32 kDa was also detected that corresponds to a homodimer of cathelin-like protein. These results demonstrated the effectiveness of the expression system used and recovery after purification (10–15 mg per 1). Full-length hCAP18/LL-37 was identically purified and confirmed by identical techniques. Cathelicidin proteins were removed from the N-terminal tag by cleavage with enterokinase.

Optimization studies found that enterokinase treatment yielded complete cleavage when digestion was carried out at 37° C. overnight. No nonspecific cleavage or degradation was observed during this period as confirmed by Coomassie blue staining of the gel (FIG. 1c, lane 2). Following enterokinase cleavage, cathelicidin proteins were further purified by size exclusion chromatography, fractions were analyzed by SDS-PAGE, and then identity and purity were confirmed by mass spectrometry (FIG. 1d). Approximately 50% of the preparations of recombinant cathelin-like protein displayed the expected peak at 11167.5 mass units by matrix-assisted laser desorption/ionization in agreement with theoretical mass and full disulfide bond formation of this protein. To further confirm the identity of hCAP18/LL-37, the recombinant protein was treated with elastase to observe if this protein was processed similarly to the native cathelicidin. Elastase treatment generated a band migrating at the same size as synthetic LL-37, and a band at 14 kDa as seen by Western blot using anti-LL-37 antibodies. This profile is similar to that observed with the previously reported experiments on native human cathelicidins isolated from neutrophils and treated with elastase or proteinase 3.

Figure 2:
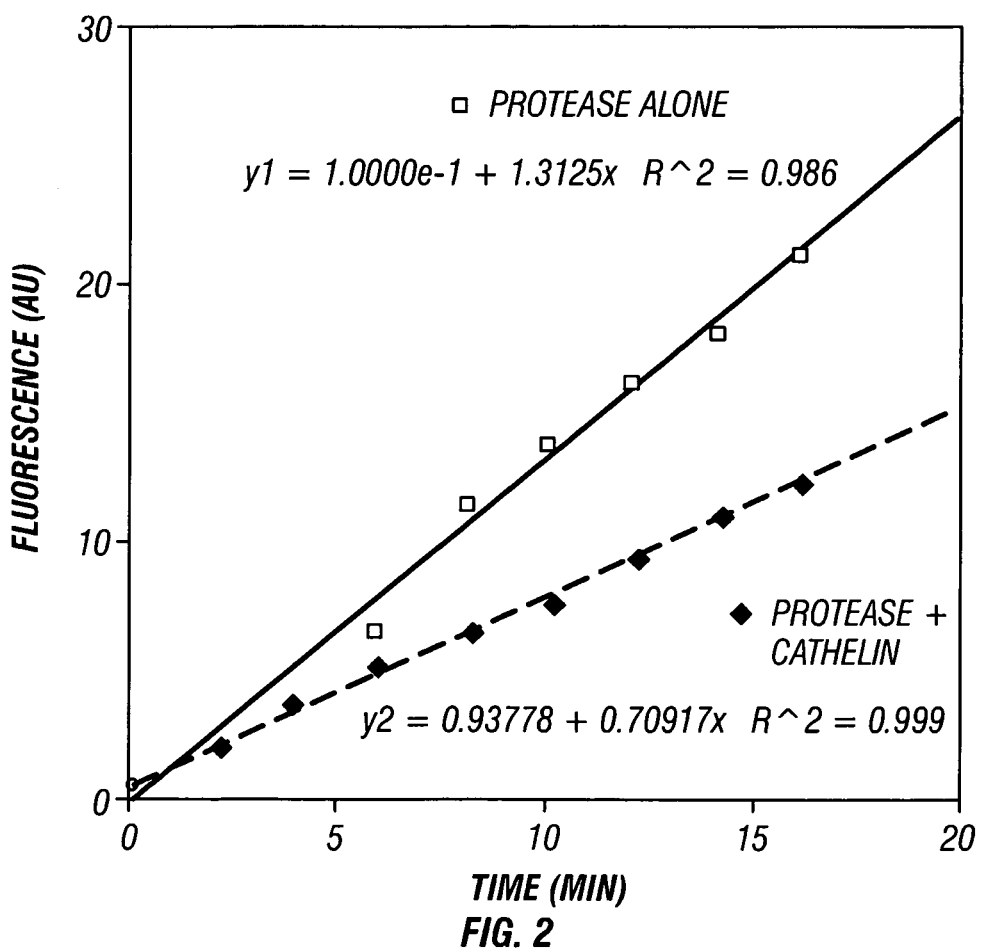
FIG. 2 show the proteinase inhibitory activity of recombinant cathelin-like protein. Hydrolysis of the fluorogenic substrate Z-Phe-Arg-AMC by cathepsin L (protease alone), and in the presence of cathelin-like protein (protease+ cathelin). Data demonstrate inhibition of cathepsin L by the addition of cathelin-like recombinant protein. Slopes, intercepts, and correlation coefficients were calculated by linear regression. Data were recorded 10 times over 30 min and are representative of two experiments.

Proteinase inhibitory activity. To evaluate the possible protease inhibitory activity action of cathelin-like protein, the activity of human cathepsin L was measured in the presence or absence of recombinant cathelin-like protein using the fluorescent substrate Z-Phe-Arg-AMC. As shown in FIG. 2, there was a linear relationship ($R^2$=0.98–99) between the control (cathepsin L alone) and the test (cathepsin L+cathelin-like protein). The generation of fluorescence was significantly decreased (slope=1.31 vs 0.71, respectively) when cathelin-like protein was added to the reaction. The hydrolytic activity of the cysteine proteinase cathepsin L was inhibited by 46% when cathelin-like protein was added at a final concentration of $10^{-6}$ M. Parallel experiments with recombinant full-length hCAP18/LL-37 did not demonstrate inhibitory activity.

Figure 3A:
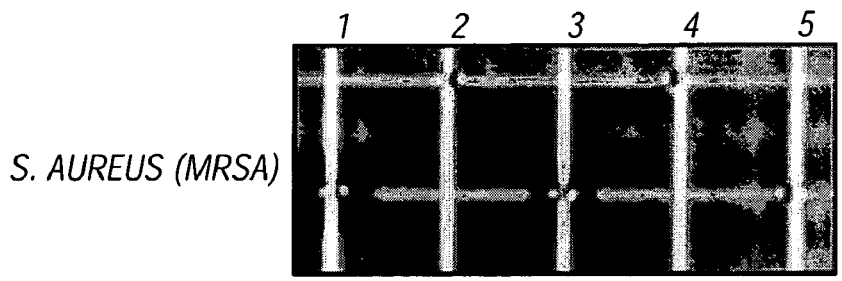
FIGS. 3A–C show Growth inhibition of MRSA, *E. coli*, and *P. aeruginosa* by cathelin-like protein. (a) Inhibition zone ssay on tryptone/agarose plates with MRSA. Clear circles show lack of bacterial growth. Lanes 1, 3, 5, bottom row: cathelin-like protein at 64 mM, 32 mM, 16 µM, respectively. Lane 2, top row:32 mM of His-tagged cathelin-like protein before cleavage. Lane 4, top: enterokinase enzyme alone. All assays were performed in duplicate and repeated three times. (b), (c) CFU assay: growth inhibition of (b) MRSA and (c) *E. coli*, cultured in 10 mM phosphate and 1% TSB (pH 7.4) and then supplemented with different concentrations of human cathelin-like protein.

Antimicrobial activity of recombinant cathelin-like protein. Recombinant cathelicidins were tested for antimicrobial activity using a standard radial diffusion assay. Different concentrations of the cathelin-like protein were loaded into wells on assay plates containing Gram-positive MRSA, *S. epidermidis*, and strains of the Gram-negative bacterial species *E. coli*, *S. enteritidis*, *P. vulgaris*, and *P. aeruginosa*. Cathelin-like protein had minimal inhibitory activity against growth of MRSA at 32 mM and at 16 mM in *E. coli*, but did not inhibit growth of *P. aeruginosa* (FIG. 3a). Similarly, cathelin-like protein inhibited growth of *S. epidermidis* (32 mM) but not *S. enteritidis* or *P. vulgaris*. The full-length recombinant cathelicidin hCAP18/LL-37 did not demonstrate inhibitory activity against any of the bacteria tested, even at concentrations greater than 64 mM. In contrast to cathelin-like protein, the C-terminal peptide domains of the human and mouse cathelicidins (LL-37 and CRAMP, respectively) were inactive against the Gram-positive bacteria tested in this assay system, but were highly active against *E. coli, P. aeruginosa*, and *S. enteritidis*.

Figure 3B:
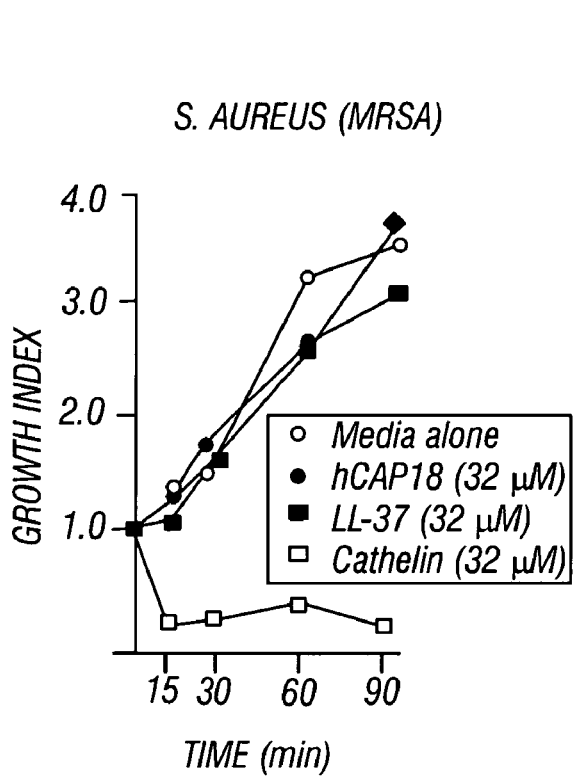
Figure 3C:
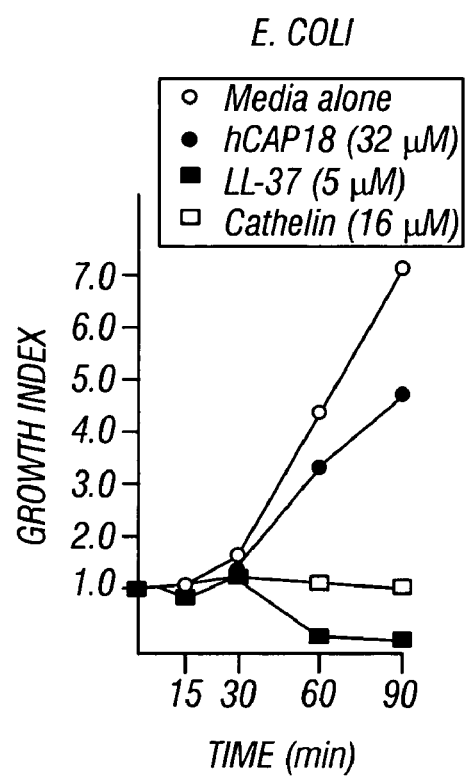

Next the cathelin-like protein was tested in a standard liquid phase AMP testing assay to validate the observed activities on agar (FIG. 3*b, c*). As LL-37 was active against *E. coli* but inactive against MRSA in the radial diffusion assay, whereas cathelin-like protein was active against both, these two bacteria were chosen for comparison of antimicrobial activity of full-length cathelicidin and its two distinct domains. With *E. coli*, addition of cathelin-like protein (16 mM) resulted in marked growth inhibition compared to the untreated controls, whereas LL-37 at 3 mM was bactericidal (FIG. 3*c*). With MRSA, an inverse pattern of activity was seen with cathelin-like protein and LL-37. Cathelin-like protein decreased MRSA CFU for the first 15 min and then was bacteriostatic, whereas LL-37 had no effect even at 32 mM. Full-length hCAP18/LL-37 (32 mM) did not show any activity against *E. coli* or MRSA (FIG. 3*b, c*). These results are consistent with those obtained in the radial diffusion plate assay. Taken together, the results demonstrate that cathelin-like protein possesses inherent antimicrobial activity and suggest a novel role for this protein in host defense.

Functional analysis of soluble peptide demonstrated that the recombinant cathelin-like domain possessed both antimicrobial and cysteine proteinase inhibitory activities. The cathelin-like protein caused inhibition of growth of Gram-negative (*E. coli*) and Gram-positive (*S. aureus*) bacterial species. This activity was distinct from the known antimicrobial spectrum of the mature C-terminal peptide. Human cathelin-like protein also inhibited the action of the lysosomal cysteine proteinase cathepsin L. The recombinant full-length hCAP18/LL-37 cathelicidin lacked both activities before processing. These findings suggest that the human cathelicidin gene encodes an inactive precursor (full-length hCAP18/LL-37) that, once processed by enzymes such as elastase or proteinase-3, generates two distinct antimicrobial molecules: cathelin-like protein and the mature LL-37 AMP. These data are distinct from an earlier study showing that native bovine proBac 5 isolated from bovine neutrophils can inhibit the activity of cathepsin L. Bovine pro-Bac5 closely resembles the full-length hCAP18/LL-37 that was inactive in the experiments. The data suggest that recombinant human cathelin-like protein alone is an inhibitor of cysteine proteinase cathepsin L.

Recombinant human cathelin-like protein was able to inhibit the proteolytic activity of the human cysteine proteinase cathepsin L. Theoretically, the inhibition of such microbial virulence determinants may be another adaptive function of the cathelin-like domain in innate immune defense.

Mammalian cathelicidin is produced as an inactive precursor that is proteolytically cleaved inside activated neutrophils and at epithelial sites of inflammation. Following this activation step, the active AMP and the cathelin-like domain with antimicrobial and cysteine protease inhibitor activities become available. Granule proteases such as elastase and cathepsin each play important roles in neutrophil function and resistance to infection. It is possible that protease cleavage of full-length cathelicidin into two active antimicrobial agents is a critical step in the pathway to microbial killing. The prosequence inhibition of cathepsin activity may represent a feedback loop to control the magnitude of local tissue degradation during the inflammatory process.

Motifs involved in the interaction of cystatins with cysteine proteinases are not fully conserved in the cathelin-like domain, however. For example, glycine 9 (chicken cystatin numbering), a conserved residue found in all known sequences of inhibitory cystatins, is not present in cathelin-like protein. Another highly conserved sequence, QXVXG (SEQ ID NO:10) (residues 53–57), is also not present, indicating that the interaction with cysteine proteinases is different. Overall, the proteinase inhibition activity of cathelin-like protein may be an alternative strategy of the host to control the regulation of its own enzymes and also to defend itself against microbe proteinases.

The results with recombinant cathelin-like peptide from these studies displayed antimicrobial activity at concentrations ranging from 16 to 32 μM against bacteria resistant to LL-37. Cathelin-like protein caused growth inhibition of both Gram-negative (*E. coli*) and Gram-positive (*S. aureus*) bacteria.

Many cationic and amphipathic peptides such as indolicidin and magainins exert their antimicrobial activity through membrane disruption and pore forming. Cathelin-like protein is not a basic protein, however, and therefore the mechanism of antimicrobial action is probably different from this class of peptides.

One possibility is that cathelin-like protein has structural features that interact with the microbial membrane. Based on the proposed three-dimensional structure of the prosequence of the porcine protegrin-type cathelicidin, the N-terminus of this molecule presents an a-helical structure. This structure could be involved in the disruption of the normal function of microbial membrane. Furthermore, cystatins are similar to cathelin-like proteins, are not basic proteins, and also show antibacterial and antiviral activity against a range of organisms. A synthetic peptide mimicking the cysteine proteinase inhibitory site of human cystatin C was found to kill *S. pyogenes*. Secretary leukocyte protease inhibitor is a 12 kDa protein that also contains both serine protease inhibitory and antimicrobial activities. Recently, a cysteine proteinase inhibitor, designated L-cystatin, which is stored in the large granules of horseshoe crab hemocytes, was identified. This molecule is 12,600 kDa, is similar to cystatin superfamily members, contains two disulfide bridges at positions corresponding to the cathelin-like domain, and has shown antimicrobial activity against Gram-negative bacteria.

Figure 4:
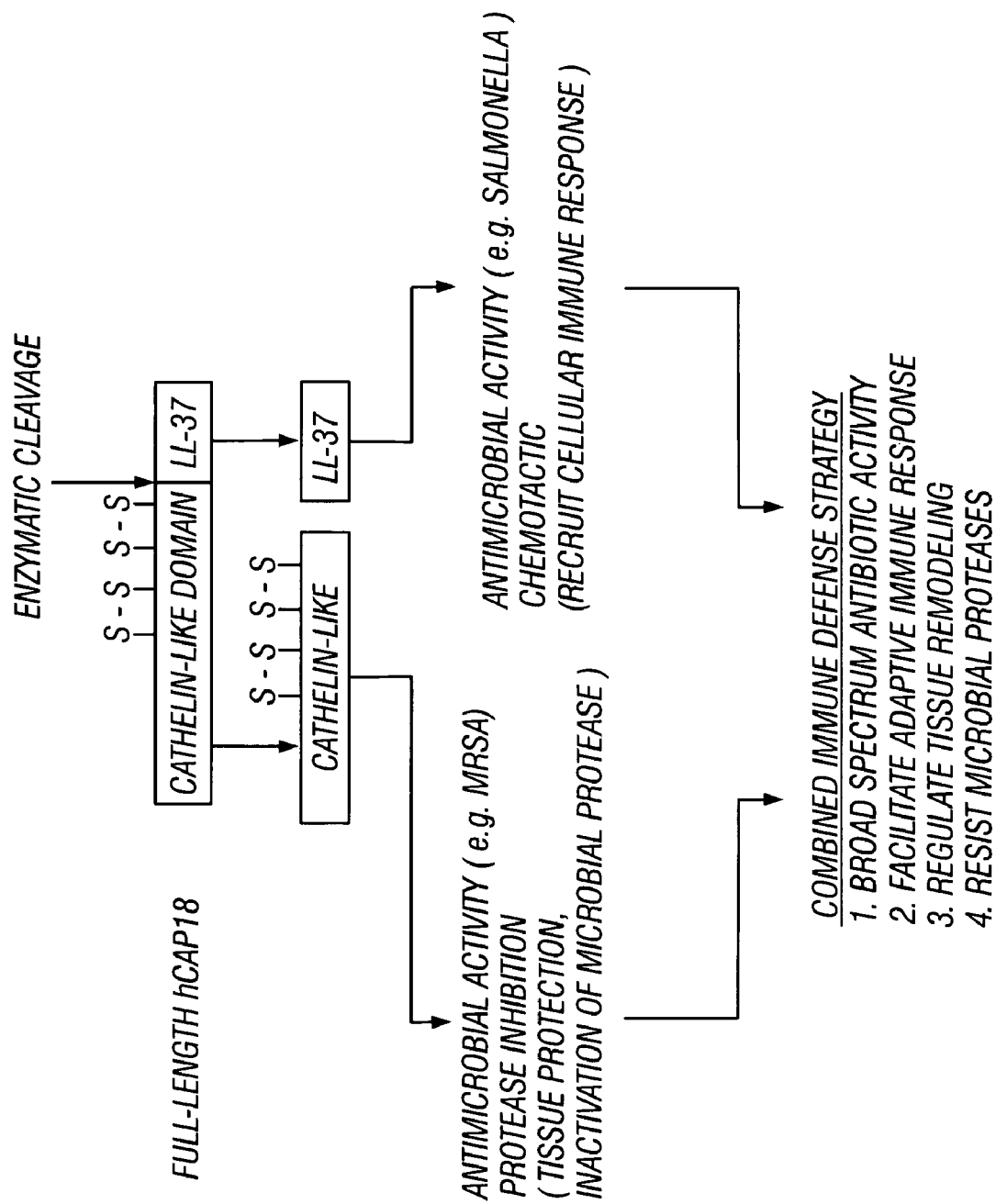
FIG. 4 shows a schematic representation of the potential actions of human cathelicidin in innate immune defense. An inactive full-length precursor is cleaved by enzymes released in the inflammatory process to yield two distinct antimicrobial peptides with complementary actions.

These structural similarities support the function proposed for the cathelin-like protein. Furthermore, a recent investigation has solved the crystal structure of a homologous domain from the porcine cathelicidin protegrin-3. These data confirm the similarity between cathelin-like proteins and cystatins, and also demonstrate potential homodimer formation for this protein as we observed in FIG. 1(*c*). The data suggest that cathelin-like protein may play important roles not only in the protection of cells from unfavorable proteolysis by host and microbial cysteine proteases, but also in the direct killing or inhibition of invading pathogens. Several functions for the peptide C-terminal domain of the cathelicidin gene product have been discovered ranging from influencing proteoglycan expression, angiogenesis, and chemotaxsis to its antimicrobial effects. This study now shows that the cathelin-like domain has multiple functions that can have complementary actions with the mature AMP in tissue defense (illustrated schematically in FIG. 4).

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A method for inhibiting the growth of a bacterium or yeast comprising contacting the bacterium or yeast with an inhibiting effective amount of a peptide consisting of an amino acid sequence as set forth in SEQ ID NO:2 from about amino acid 31 to 131.

2. The method of claim 1, wherein the bacterium is gram positive.

3. The method of claim 1, wherein the bacterium is gram negative.

4. The method of claim 1, further comprising contacting the bacterium or yeast with at least one antimicrobial agent.

5. The method of claim 4, wherein the antimicrobial agent is selected from the group consisting of a β-lactam, novobiocin, polymyxin B, and LL-37.

6. The method of claim 1, wherein the contacting is in vitro.

7. The method of claim 1, wherein the contacting is in vivo.

8. The method of claim 7, wherein the contacting is by topical administration.

9. A method for inhibiting the growth of a bacterium or yeast comprising contacting the bacterium or yeast with an inhibiting effective amount of a polypeptide selected from the group consisting of:
   a) a polypeptide consisting of amino acid residues 31 to 131 of SEQ ID NO:2 and having 1–10 conservative amino acid substitutions:
   b) a polypeptide comprising amino acid residues 31 to 131 of SEQ ID NO:2 and having 1–10 additional amino acid residues at the amino-terminus and/or carboxy-terminus wherein the additional amino acid residues are heterologous to residues 1–30 of SEQ ID NO:2 and/or residues 132–170 of SEQ ID NO:2; and
   c) a polypeptide consisting of amino acid residues $X_2$ to $X_3$, wherein $X_2$ is an amino acid residue selected from the group consisting of residues 29, 30 and 31 of SEQ ID NO:2, and wherein $X_3$ is an amino acid residue selected from the group consisting of residues 128, 129, 130 and 131 of SEQ ID NO:2, wherein the is polypeptide comprises cysteine proteinase inhibitor activity or exhibits antibacterial activity,
   or a combination thereof.

10. The method of claim 9, wherein amino acid residues 31–131 of SEQ ID NO:2 include 1–5 conservative amino acid substitutions.

11. A method for inhibiting the growth of a bacterium or yeast comprising contacting the bacterium or yeast with an inhibiting effective amount of a polypeptide selected from the group consisting of:
   a) a polypeptide comprising amino acid residues 31 to 131 of SEQ ID NO:2 including 1–10 conservative amino acid substitutions, and excluding:
      i) residues 1–30 of SEQ ID NO:2 contiguous with the amino terminus of residues 31–131 of SEQ ID NO:2; and
      ii) residues 132–170 of SEQ ID NO:2 contiguous with the carboxy-terminus of residues 31–131 of SEQ ID NO:2; and
   b) a polypeptide comprising amino acid residues 31 to 131 of SEQ ID NO:2, and excluding:
      i) residues 1–30 of SEQ ID NO:2 contiguous with the amino terminus of residues 31–131 of SEQ ID NO:2; and
      ii) residues 132–170 of SEQ ID NO:2 contiguous with the carboxy-terminus of residues 31–131 of SEQ ID NO:2; wherein residues 31–131 of SEQ ID NO:2 comprise cysteine proteinase inhibitor activity or antibacterial activity, or a combination thereof.

* * * * *